(12) United States Patent
Hirohara et al.

(10) Patent No.: US 6,685,320 B2
(45) Date of Patent: Feb. 3, 2004

(54) OPTHALMIC CHARACTERISTIC MEASURING APPARATUS

(75) Inventors: Yoko Hirohara, Tokyo (JP); Toshifumi Mihashi, Tokyo (JP); Koki Harumoto, Tokyo (JP)

(73) Assignee: Kabushiki Kaisha Topcon, Tokyo (JP)

(*) Notice: Subject to any disclaimer, the term of this patent is extended or adjusted under 35 U.S.C. 154(b) by 88 days.

(21) Appl. No.: 10/122,223

(22) Filed: Apr. 16, 2002

(65) Prior Publication Data

US 2002/0163623 A1 Nov. 7, 2002

(30) Foreign Application Priority Data

Apr. 18, 2001 (JP) .................................. 2001-120046

(51) Int. Cl.⁷ .................................................. A61B 3/10
(52) U.S. Cl. ...................................... 351/221; 351/212
(58) Field of Search .............................. 351/205, 206, 351/211, 212, 221, 246; 606/4, 5

(56) References Cited

U.S. PATENT DOCUMENTS 6,382,796 B1 * 5/2002 Ban ............................ 351/212
6,428,168 B2 * 8/2002 Sarver et al. ................ 351/212
6,575,573 B2 * 6/2003 Lai et al. ..................... 351/212

* cited by examiner

Primary Examiner—George Manuel
(74) Attorney, Agent, or Firm—Foley & Lardner

(57) ABSTRACT

A first signal and a second signal are captured at the same time, and the optical characteristics of a subject eye and the corneal shape thereof are measured simultaneously or substantially simultaneously. A calculation section captures a received light signal (first signal) from a first light receiving section and a received light signal (second signal) from a second light receiving section at the same timing or substantially the same timing, obtains the optical characteristics of the subject eye on the basis of the first signal, and obtains the corneal shape of the subject eye on the basis of the second signal. A measurement timing decision section decides, on the basis of the first and/or the second signal, measurement timings of the first signal and the second signal as objects for which a measurement calculation is carried out. The measurement timing decision section uses, as a predetermined decision factor for measuring timing, at least one of a blink, a poor tear film, a lack of a pupil diameter, and a poor eyelid. A display section displays, as an image, the first signal and/or the second signal. The operator judges, on the basis of the displayed first signal and/or second signal, suitableness of measurement with the predetermined decision factor for measuring timing, and decides a measurement signal used for the calculation section.

10 Claims, 16 Drawing Sheets

TABLE SHOWING ELEMENTS DETECTED WITH FIRST SIGNAL AND SECOND SIGNAL

|  | BLINK | TEAR FILM | PUPIL DIAMETER | EYELID OPENING | FIXATION STATE |
|---|---|---|---|---|---|
| FIRST SIGNAL | ○ | ○ | ○ | △ | × |
| SECOND SIGNAL | ◎ | ◎ | ◎ | ◎ | ○ |

EXPLANATORY NOTES: ○···POSSIBLE   ◎···GOOD   ×···IMPOSSIBLE

271

TABLE SHOWING ADAPTABLE CONDITIONS WHEN SAME ELEMENT IS DETECTED WITH DIFFERENT SIGNALS

| FIRST * SECOND SIGNAL | ◎ | ◎ | ◎ | ◎ | × |
|---|---|---|---|---|---|

272

TABLE SHOWING ADAPTABLE CONDITIONS WHEN DIFFERENT ELEMENT OR SAME ELEMENT IS DETECTED WITH DIFFERENT SIGNALS

| | | SECOND SIGNAL | | | | |
|---|---|---|---|---|---|---|
| | | BLINK | TEAR FILM | PUPIL DIAMETER | EYELID OPENING | FIXATION STATE |
| FIRST SIGNAL | INTERNAL ABERRATION | ○ | ○ | ○ | ○ | ○ |
| | BLINK | ◎ | ○ | ○ | ○ | ○ |
| | TEAR FILM | ○ | ◎ | ○ | ○ | ○ |
| | PUPIL DIAMETER | ○ | ○ | ◎ | ○ | ○ |
| | EYELID OPENING | ○ | ○ | ○ | ◎ | ○ |
| | FIXATION STATE | — | — | — | — | — |

274
275
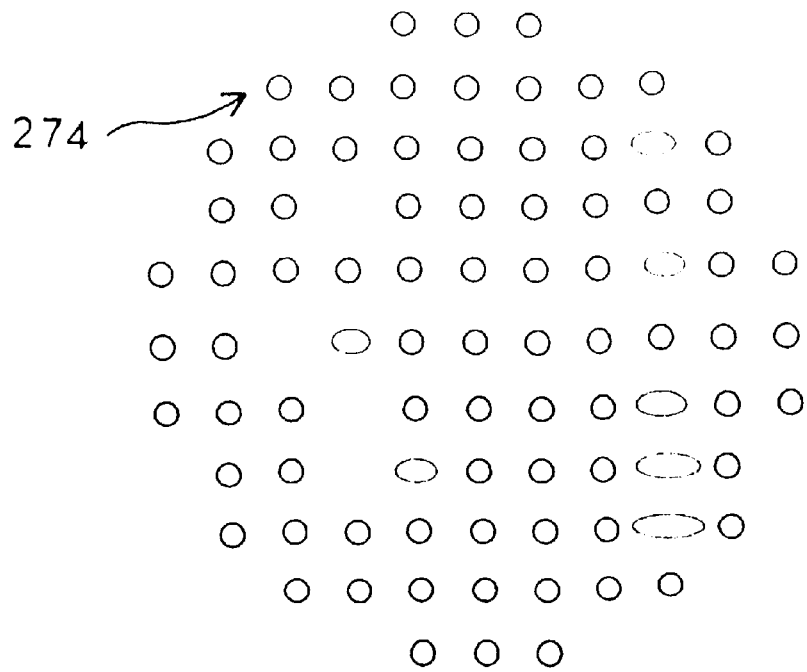
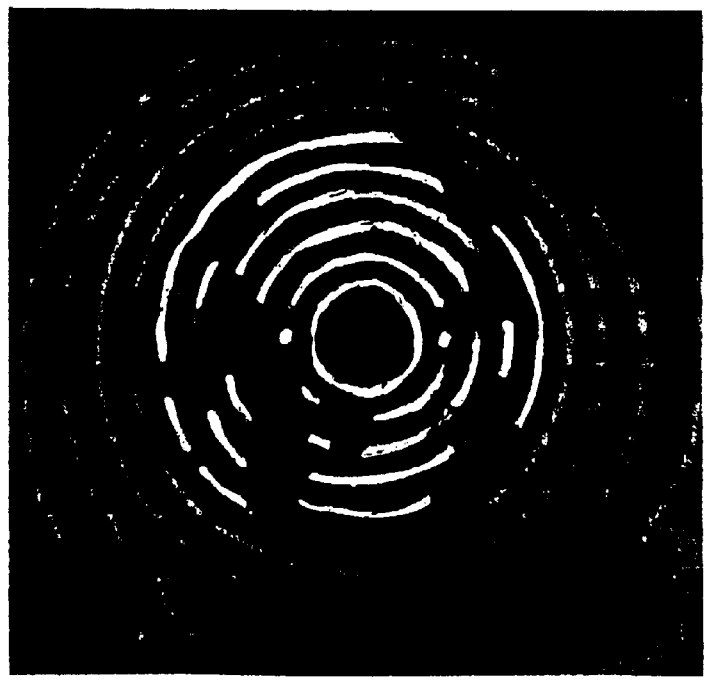
Fig. 6

CORNEAL HIGHER ORDER ABERRATION MAP
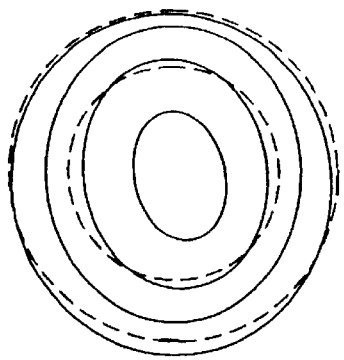
(A)
OCULAR HIGHER ORDER ABERRATION MAP
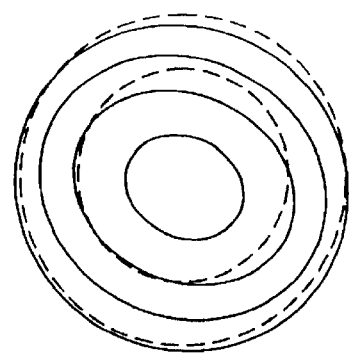
(B)
DIFFERENTIAL HIGHER ORDER ABERRATION MAP
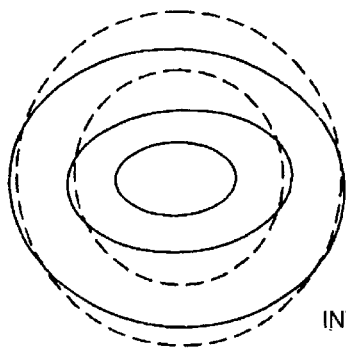
INTERNAL ABERRATIONS
(C)
Fig. 9

Fig. 16

OPTHALMIC CHARACTERISTIC MEASURING APPARATUS

BACKGROUND OF THE INVENTION

The present invention relates to an ophthalmic characteristic measuring apparatus, and particularly to an ophthalmic characteristic measuring apparatus in which before the optical characteristics of a subject eye, the corneal shape of the subject eye and the like are calculated, data suitable for the calculation can be more accurately selected by visual confirmation.

In recent years, optical instruments used for medicine have had extremely various applications. Particularly, in ophthalmology, the optical equipment has come into wide use as an optical characteristic measuring apparatus for examining ophthalmic functions such as refraction of an eye or adjustment thereof and the inside of an eyeball. In the measurement results of various examinations, it is important that the patient's eye to be measured as the object of examination is put in what kind of decision factor for measuring timing.

In general, cornea topography is effective for many uses, for example, an estimate of result of an operation such as keratotomy or keratectomy, clinical test after corneal transplant, design and evaluation of a contact lens for myopia/hyperopia, and diagnosis/disease judgment of a cornea. As a conventional method of measuring the corneal shape, there is, for example, a placido disk technique, a stereogram technique, a moire technique, a topography interferometric technique or the like.

As the optical characteristic measuring apparatus, for example, there is known an apparatus in which light of a point light source is projected onto an eye-ground, is converted into a predetermined number of beams by a converting member such as a Hartmann plate, and the beams are received by a light receiving section to measure the optical characteristics of the eye, or a corneal shape measuring apparatus for measuring the corneal shape by using placido's disc with visible light. Incidentally, in the present specification, a signal obtained through the Hartmann plate and needed to measure the optical characteristics of the eye to be measured is made a first signal, and a signal obtained through the placido's disc and needed to measure the corneal shape of the eye to be measured is made a second signal.

When the ophthalmic characteristics are calculated, the measured first signal and second signal are not necessarily suitable.

Besides, in general, at the point of time when alignment is adjusted manually or automatically, a measurement is manually or automatically started. A coordinate system (CCD coordinate) incident to a CCD at the time of the measurement corresponds to a CCD coordinate at the side of an opposite object (eye side) through the CCD and lens. Although a Hartmann wavefront sensor measurement (first measurement system) and a corneal shape measurement (second measurement system) are made almost simultaneously in the respective CCDs, there is a case where the measurements are not made strictly at the same time. Thus, in the measurements, a main cause is, for example, movement of the eye, and it is not assured that the CCD coordinate system of the first measurement system becomes equal to the CCD coordinate of the second measurement system. It has been already carried out that the edge of a pupil is obtained from an anterior eye image and is used for the alignment. However, in the case where the acquisition timing of the Hartmann image is not completely coincident with the acquisition timing of the anterior eye alignment image, if the alignment is made by only the anterior eye alignment image, there is a possibility that a deviation occurs in the alignment of the Hartmann measurement by ocular movement, etc. As stated above, it is supposed that it is difficult for the conventional optical characteristic measuring apparatus to simultaneously measure the optical characteristics of the eye to be measured and its corneal shape.

SUMMARY OF THE INVENTION

In view of the above, an object of the present invention is to provide an ophthalmic characteristic measuring apparatus including wavefront measurement in which data processing is effectively carried out. Particularly, the invention has an object to enable selection of data suitable for calculation by visual confirmation before the calculation of optical characteristics of the subject eye and the corneal shape of the subject eye.

Besides, another object of the invention is to provide a structure suitable for capturing a first signal of a first measurement system and a second signal of a second measurement system simultaneously or substantially simultaneously.

Besides, still another object of the invention is to provide a structure suitable for continuously capturing the first signal and the second signal simultaneously or substantially simultaneously.

Besides, still another object of the invention is to make a measurement at the time when the first signal and the second signal come to have states suitable for the measurement.

Besides, still another object of the invention is to make a measurement such that when there are a plurality of factors to influence the measurement, the suitableness of those factors is judged with signals which can respectively detect them with ease, and the measurement timing is determined, so that the measurement is made in the state where a highly reliable measurement result can be obtained.

According to the invention, an ophthalmic characteristic measuring apparatus comprises:
  a first light source for emitting a first light flux of a first wavelength of near infrared;
  a first illumination optical system for illuminating a minute region on a retina of a subject eye with the light flux from the first light source;
  a first light receiving optical system for receiving a part of a first reflected light flux of the first light flux from the first light source, reflected from the retina of the subject eye, through a first conversion member for converting it into at least 17 beams;
  a first light receiving section for receiving a first received light flux guided by the first light receiving optical system to form a first signal;
  a second light source section for emitting a second light flux of near infrared having a second wavelength longer than the first wavelength of the first light flux;
  a second illumination optical system for illuminating a vicinity of the cornea of the subject eye with the second light flux from the second light source and with a predetermined pattern;
  a second light receiving optical system for receiving a second reflected light flux of the second light flux from the second light source, reflected from the vicinity of the cornea of the subject eye;

a second light receiving section for receiving a second received light flux guided by the second light receiving optical system to form a second signal;

a display section for displaying, as an image, the first and/or the second signal from the first light receiving section and/or the second light receiving section;

an input section for selecting the first and/or the second signal used for a calculation processing on the basis of an image display of the first and/or the second signal displayed on the display section; and a calculation section for obtaining optical characteristics of the subject eye and a corneal shape of the subject eye on the basis of first and second signals corresponding to the first and/or the second signal selected by the input section.

One of the features of the invention is that, for example, the optical characteristics of the subject eye (for example, refractivity) is measured on the basis of the first signal from the first light receiving section (or a tilt of the light flux obtained by the first light receiving section), and the corneal shape is measured on the basis of the second signal from the second light receiving section. Another feature of the invention is that for example, the first signal and the second signal can be captured simultaneously or simultaneously and continuously several times without miosis of the subject eye. Another feature of the invention is that for example, the timing of capturing the first signal and the second signal suitable for the measurement can be determined. Another feature of the invention is that for example, separate factors are judged with the first signal and the second signal, or plural factors are judged only with the first signal or the second signal, whereas important factors (for example, blink) can be judged using both the first signal and the second signal.

BRIEF DESCRIPTION OF THE DRAWINGS

FIG. 5 is an explanatory view of decision factors for measuring timing relating to a first signal and a second signal.

FIG. 6 is an explanatory view of an image received by first and second light receiving sections.

FIG. 9 is an explanatory view relating to ophthalmic characteristic measurement.

FIG. 16 is an explanatory view of an image display.

DETAILED DESCRIPTION OF THE PREFERRED EMBODIMENTS

Hereinafter, embodiments of the present invention will be described in detail with reference to the drawings.

Figure 1:
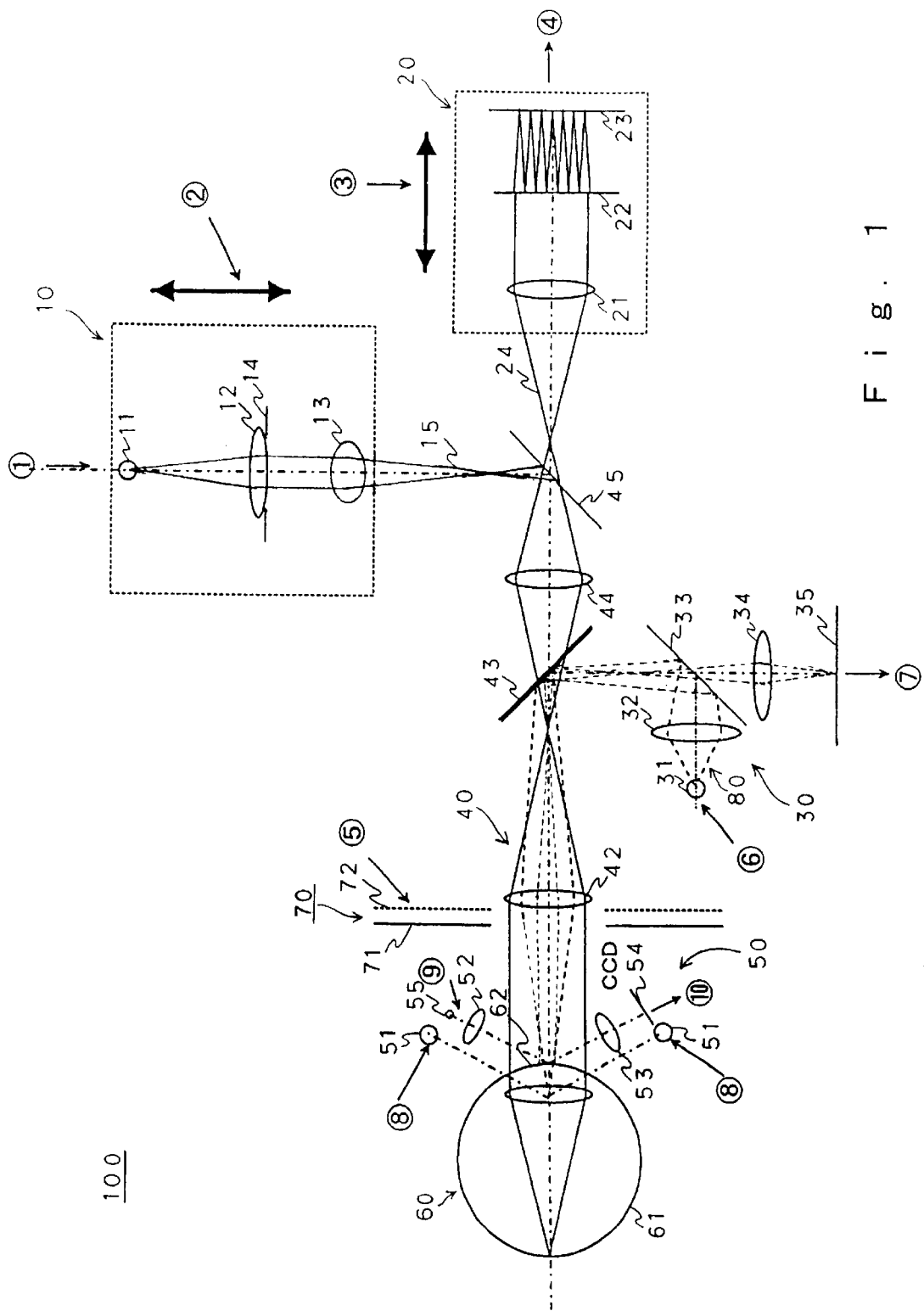
FIG. 1 is a view schematically showing an optical system 100 of an ophthalmic optical characteristic measuring apparatus of the invention.

FIG. 1 is a view schematically showing an optical system 100 of an ophthalmic optical characteristic measuring apparatus of the invention.

The optical system 100 of the ophthalmic optical characteristic measuring apparatus is, for example, an apparatus for measuring the optical characteristics of an eye 60 to be measured as an object, and includes a first illumination optical system 10, a first light receiving optical system 20, a second light receiving optical system 30, a common optical system 40, an adjusting optical system 50, a second illumination optical system 70, and a second light sending optical system 80. Incidentally, with respect to the eye 60 to be measured, a retina 61 and a cornea 62 are shown in the drawing.

The first illumination optical system 10 includes, for example, a first light source section 11 for emitting a light flux of a first wavelength, and a condensing lens 12, and is for illuminating a minute region on the retina (eyeground) 61 of the eye 60 to be measured by the light flux from the first light source section 11 so that the illumination conditions can be suitably set. Incidentally, here, as an example, the first wavelength of the light flux for illumination emitted from the first light source section 11 is a wavelength of an infrared range (for example, 840 nm, 780 nm, etc.).

It is desirable that the first light source section 11 has a large spatial coherence and a small temporal coherence. Here, the first light source section 11 is, for example, a super luminescence diode (SLD), and a point light source having high luminance can be obtained. Incidentally, the first light source section 11 is not limited to the SLD, and for example, even a laser having a large spatial coherence and temporal coherence can be used by inserting a rotational diffusion plate to suitably lower the temporal coherence. Further, even an LED having a small spatial coherence and temporal coherence can be used by, if light quantity is sufficient, inserting a pinhole or the like at the position of a light source of a light path.

The first light receiving optical system 20 includes, for example, a collimate lens 21, a Hartmann plate 22 as a conversion member for converting a part of a light flux (first light flux) reflected and returned from the retina 61 of the eye 60 to be measured into at least 17 beams, and a first light receiving section 23 for receiving the plural beams converted by the Hartmann plate 22, and is for guiding the first light flux to the first light receiving section 23. Here, a CCD with low lead-out noise is adopted for the first light receiving section 23, and as the CCD, a suitable type one, for example, a general low noise type one or a cooling CCD of 1000*1000 elements for measurement can be applied.

Figure 2:
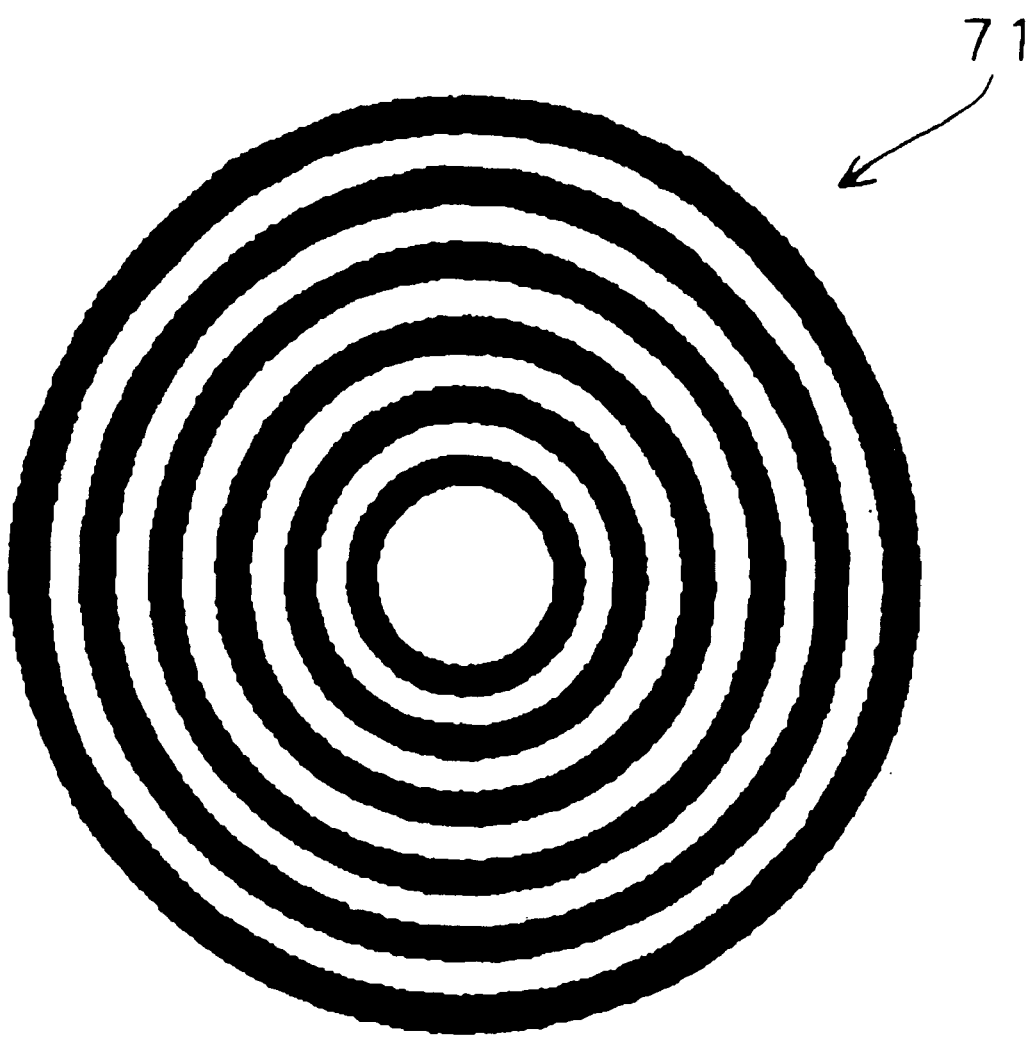
FIG. 2 is a structural view showing an example of a placido's disc.

The second illumination optical system 70 includes a second light source 72 and a placido's disc 71. Incidentally, the second light source 72 can be omitted. FIG. 2 shows an example of a structural view of the placido's disc. The placido's disc 71 is f or projecting an index of a pattern made of plural co-axial rings. Incidentally, the index of the pattern made of the plural co-axial rings is an example of indexes of predetermined patterns, and another suitable pattern can be used. After alignment adjustment described later is completed, the index of the pattern made of the plural co-axial rings can be projected.

The second light sending optical system 80 is for mainly performing, for example, after-mentioned alignment adjustment, and measurement and adjustment of a coordinate origin and a coordinate axis, and includes a second light source section 31 for emitting a light flux of a second wavelength, a light condensing lens 32, and a beam splitter 33.

The second light receiving optical system 30 includes a condensing lens 34, and a second light receiving section 35. The second light receiving optical system 30 guides a light flux (second light flux) of the pattern of the placido's disc 71 illuminated from the second illumination optical system 70, and reflected and returned from the anterior eye part or the cornea 62 of the eye 60 to be measured, toward the second light receiving section 35. Besides, it can also guide a light flux emitted from the second light source 31, and reflected and returned from the cornea 62 of the eye 60 to be measured, toward the second light receiving section 35. Incidentally, the second wavelength of the light flux emitted from the second light source section 31 is different from, for example, the first wavelength (here, 840 nm), and a wavelength (for example, 940 nm) longer than that can be selected.

The common optical system 40 is disposed on the optical axis of the light flux emitted from the first illumination optical system 10, and can be included in common in the first and second illumination optical systems 10 and 70, the first and second light receiving optical systems 20 and 30, and the second light sending optical system 80. The common optical system includes, for example, an a focal lens 42, beam splitters 43 and 45, and a condensing lens 44. The beam splitter 43 is formed of such a mirror (for example, a dichroic mirror) that the wavelength of the second light source section 31 is sent (reflected) to the eye 60 to be measured, and the second light flux reflected and returned from the retina 61 of the eye 60 to be measured is reflected, whereas the wavelength of the first light source 11 is transmitted. The beam splitter 45 is formed of such a mirror (for example, dichroic mirror) that the wavelength of the first light source section 11 is sent (reflected) to the eye 60 to be measured, and the first light flux reflected and returned from the retina 61 of the eye 60 to be measured is transmitted. The beam splitters 43 and 45 prevent the first and the second light fluxes from entering different optical systems and generating noise.

The adjusting optical system 50 mainly performs, for example, a working distance adjustment described later, and includes a third light source section 51, a fourth light source section 55, condensing lenses 52 and 53, and a third light receiving section 54.

Next, the alignment adjustment will be described. The alignment adjustment is mainly carried out by the second light receiving optical system 30 and the second light sending optical system 80.

First, the light flux from the second light source section 31 illuminates the eye 60 to be measured as the object with the substantially parallel light flux through the condensing lens 32, the beam splitters 33 and 43, and the a focal lens 42. The reflected light flux reflected by the cornea 62 of the eye 60 to be measured is emitted as a divergent light flux as if it is emitted from a point of ½ of the radius of curvature of the cornea 62. This divergent light source is received as a spot image by the second light receiving section 35 through the a focal lens 42, the beam splitters 43 and 33, and the condensing lens 34.

Here, in the case where the spot image on the second light receiving section 35 is deviated from the light axis, the body of the ophthalmic optical characteristic measuring apparatus is moved and adjusted vertically and horizontally to make the spot image coincident with the light axis. When the spot image coincides with the optical axis in this way, the alignment adjustment is completed. Incidentally, when the cornea 62 of the eye 60 to be measured is illuminated with a third light source section 51, an image of the eye 60 to be measured obtained by this illumination is formed on the second light receiving section 35, and accordingly, the alignment adjustment may be made such that this image is used to make the pupil center coincident with the optical axis.

Next, the working distance adjustment will be described. The working distance adjustment is carried out mainly by the adjusting optical system 50.

First, the working distance adjustment is carried out in such a manner that the parallel light flux in the vicinity of the optical axis emitted from the fourth light source section 55 is illuminated to the eye 60 to be measured, and the light reflected from this eye 60 to be measured is received by the third light receiving section 54 through the condensing lenses 52 and 53. In the case where the eye 60 to be measured is within a suitable working distance, a spot image from the fourth light source section 55 is formed on the optical axis of the third light receiving section 54. On the other hand, in the case where the eye 60 to be measured is outside the suitable working distance in front and rear, the spot image from the fourth light source 55 is formed above or below the optical axis of the third light receiving section 54. Incidentally, since it is sufficient if the third light receiving section 54 can detect the change of the light flux position on the plane including the fourth light source section 55, the optical axis, and the third light receiving section 54, for example, a one-dimensional CCD disposed on this plane, a position sensing device (PSD) or the like can be applied.

Next, the positional relation between the first illumination optical system 10 and the first light receiving optical system 20 will be roughly described.

The beam splitter 45 is inserted in the first light receiving optical system 20, and by this beam splitter 45, the light from the first illumination optical system 10 is sent to the eye 60 to be measured, and the reflected light from the eye 60 to be measured is transmitted. The first light receiving section 23 included in the first light receiving optical system 20 receives the light transmitted through the Hartmann plate 22 as the conversion member and generates a received light signal.

The first light source section 11 and the retina 61 of the eye 60 to be measured form a conjugate relation. The retina 61 of the eye 60 to be measured and the first light receiving section 23 are conjugate with each other. The Hartmann plate 22 and the pupil of the eye 60 to be measured form a conjugate relation. That is, the front side focus of the a focal lens 42 is substantially coincident with the pupil of the eye 60 to be measured.

The first illumination optical system 10 and the first light receiving optical system 20 are moved together so that on the assumption that the light flux from the first light source 11 is reflected at the condensed point, a signal peak by the reflected light at the first light receiving section 23 becomes maximum. Specifically, the first illumination optical system 10 and the first light receiving optical system 20 move in the direction that the signal peak at the first light receiving section 23 becomes large, and stop at the position where the signal peak becomes maximum. By this, the light flux from the first light source section 11 is condensed on the eye 60 to be measured.

The lens 12 converts the diffused light of the light source 11 into parallel light. A diaphragm 14 is put at a position optically conjugate with the pupil of the eye or the Hartmann plate 22. In the diaphragm 14, its diameter is smaller than the effective range of the Hartmann plate 22, and so-called single path aberration measurement (a method in which aberration of an eye influences only the light receiving side) is established. A lens 13 is disposed such that an eyeground conjugate point of a real light beam is at the front side focal position to satisfy the above, and further, the rear side focal position is coincident with the diaphragm 14 to satisfy the conjugate relation to the pupil of the eye.

After a light beam 15 comes to have an optical path common to a light beam 24 by the beam splitter 45, it approximately advances in the same way as the light beam 24. At the time of single path measurement, the diameters of the respective light beams are different from each other, and the beam diameter of the light beam 15 is set to be rather thinner than the light beam 24. Specifically, the beam diameter of the light beam 15 is, for example, about 1 mm at the position of the pupil of the eye, and the beam diameter of the light beam 24 becomes about 7 mm (incidentally, in the drawing, the light beam 15 from the beam splitter 45 to the eyeground 61 is omitted.

Next, the Hartmann plate 22 as the conversion member will be described.

The Hartmann plate 22 included in the first light receiving optical system 20 is a wavefront conversion member for converting a reflected light flux into plural beams. Here, plural micro Fresnel lenses disposed in the plane orthogonal to the optical axis are applied for the Hartmann plate 22. In general, with respect to a measurement object (the eye 60 to be measured), in order to measure a spherical component of the eye 60 to be measured, third astigmatism, and the other higher order aberration, it is necessary to make a measurement with at least 17 beams through the eye 60 to be measured.

The micro Fresnel lens is an optical element, and includes, for example, rings of height pitch for each wavelength and blades optimized for emission parallel with condensing point. The micro Fresnel lens here is provided with light path length differences of eight levels in which a semiconductor minute working technique is applied, and achieves a high condensing rate (for example, 98%)

The reflected light from the retina 61 of the eye 60 to be measured passes through the a focal lens 42 and the collimate lens 21, and is condensed onto the first light receiving section 23 through the Hartmann plate 22. Accordingly, the Hartmann plate 22 includes the wavefront conversion member for converting the reflected light flux into at least 17 beams.

Figure 3:
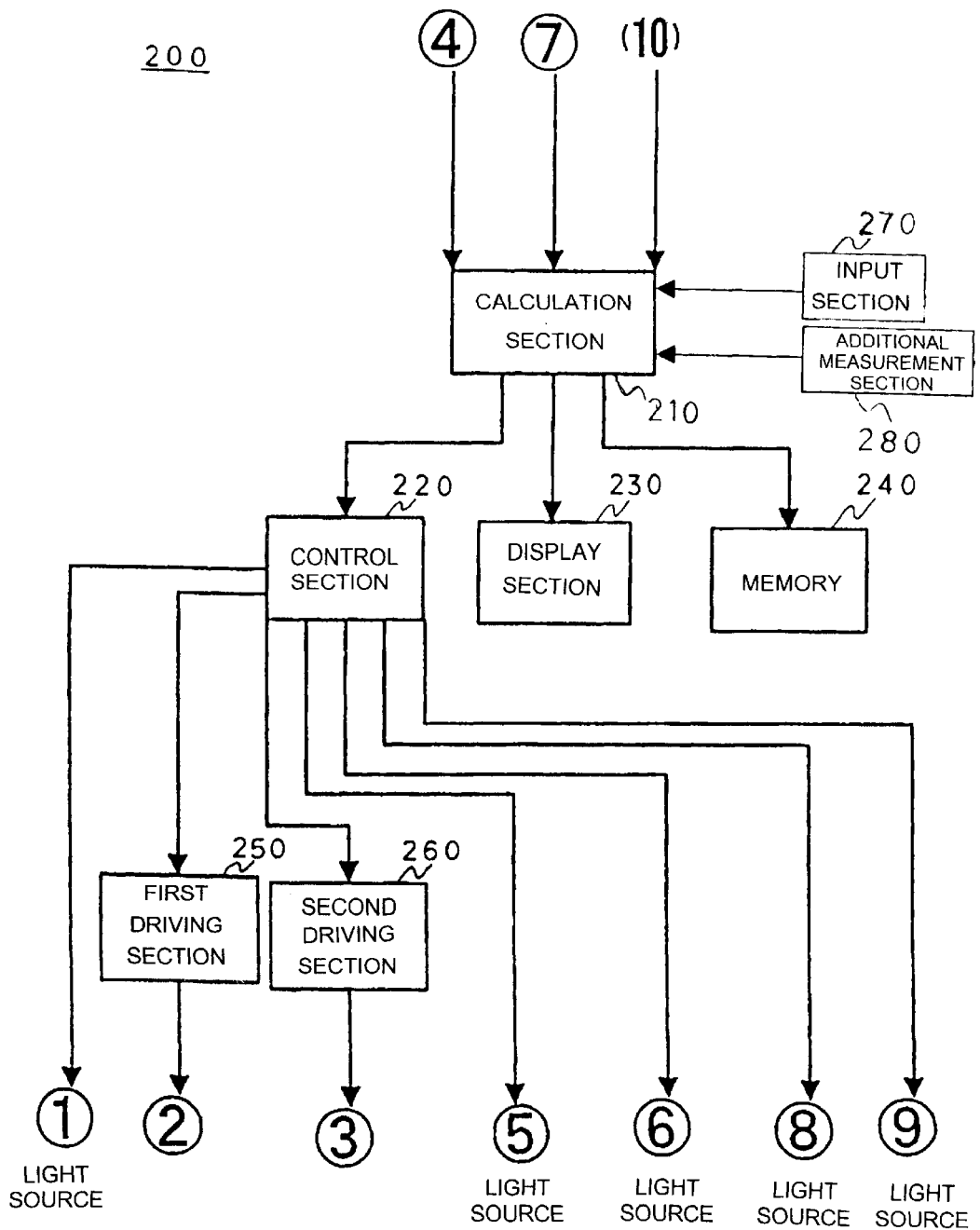
FIG. 3 is a block diagram schematically showing an electric system 200 of the ophthalmic optical characteristic measuring apparatus of the invention.

FIG. 3 is a block diagram schematically showing an electric system 200 of the ophthalmic optical characteristic measuring apparatus of the invention.

The electric system 200 of the ophthalmic optical characteristic measuring apparatus includes, for example, a calculation section 210, a control section 220, a display section 230, a memory 240, a first driving section 250, a second driving section 260, an input section 270, and an additional measurement section 280.

The calculation section 210 captures the first and the second signals from the first light receiving section 23 and the second light receiving section 35 at the same timing or substantially the same timing, obtains the optical characteristics of the subject eye on the basis of the first signal from the first light receiving section 23, and obtains the corneal shape of the subject eye on the basis of the second signal from the second light receiving section 35. Here, the calculation section 210 obtains the optical characteristics of the subject eye and the corneal shape of the subject eye on the basis of the first and the second signals selected by the input section 270. The calculation section 210 receives a received light signal (first signal) ④ obtained from the first light receiving section 23, a received light signal (second signal) ⑦ obtained from the second light receiving section 35, and a received light signal ⑩ obtained from the third light receiving section 54, and calculates a coordinate origin, a coordinate axis, movement of a coordinate, rotation, ocular aberration, corneal aberration, Zernike coefficients, aberration coefficients, Strehl ratio, white light MTF, Landolt's ring pattern, and the like. Further, the calculation section outputs signals corresponding to the calculation results to the control section 220 for controlling the whole of the electric driving system, the display section 230, and the memory 240. Further, the calculation section 210 obtains a measurable period with the first signal, the second signal, or both the first signal and the second signal and on the basis of the decision factor for measuring timing. The calculation section 210 can select a continuous measurement mode, and in the continuous measurement mode, in the case where measurement adaptable conditions of the first signal or the second signal are satisfied, measurements of the first signal and the second signal can be made at predetermined intervals. Besides, in the continuous measurement mode, in the case where the measurement adaptable conditions of the first signal or the second signal are again satisfied, the calculation section 210 can automatically make measurements. Further, the calculation section 210 can select (change) a learning mode (for example, learning mode concerning measurement timing). In the case where the learning mode is selected, a measurement adaptable condition at the measurement is stored, and maybe reflected for the setting of the measurement adaptable conditions of the first signal or the second signal. In this learning mode, for example, the learning mode is turned ON at the time of measurement by a skilled person, and the measurement timing at that time is stored, and when the measurable period is set, a period after a predetermined time has passed from a blink may be referred to. Besides, the calculation section 210 stores a signal of the second light receiving section at the measurement, and enables the signal of the second light receiving section to be displayed on the display section 230, together with measurement data. The calculation section 210 correlates, for example, an anterior eye image at the measurement with the measurement result and stores them in the memory 240, and can display the anterior eye image and the measurement result on the display section 230. The details of the calculation section 210 are described later.

The control section 220 controls switching on and off of the first light source section 11 on the basis of the control signal from the calculation section 210, and controls the first driving section 250 and the second driving section 260. For example, on the basis of the signal corresponding to the calculation result in the calculation section 210, the control section outputs a signal ① to the first light source section 11, outputs a signal ⑤ to the placido's disc 71, outputs a signal ⑥ to the second light source section 31, outputs a signal ⑧ to the third light source section 51, outputs a signal ⑨ to the fourth light source section 55, and outputs signals to the first driving section 250 and the second driving section 260.

The first driving section 250 moves to the optical axis direction, for example, the whole of the first illumination optical system 10 on the basis of the received light signal ④ inputted to the calculation section 210 from the first light receiving section 23, outputs a signal ② to a not-shown suitable lens moving unit, and drives the lens moving unit. By this, the first driving section 250 can move and adjust the first illumination optical system 10.

The second driving section 260 moves to the optical axis direction, for example, the whole of the first light receiving optical system 20 on the basis of the received light signal ④ inputted to the calculation section 210 from the first light receiving section 23, and outputs a signal ③ to the not-shown suitable lens moving unit, and drives the lens moving unit. By this, the second driving section 260 can move and adjust the first light receiving optical system 20.

The input section 270 is for making various selections of, for example, a measurement mode, a decision factor for measuring timing, a measurable period (range), the number of times of continuous measurement in the case of a continuous mode, and the like. The measurement mode is for selecting automatic or manual mode, single measurement or continuous measurement, and the like. In the case where the manual mode is selected as the measurement mode, the input section 270 becomes, for example, a finder switch for manual measurement. With respect to the decision factor for measuring timing, the received light signal (first signal) ④ obtained from the first light receiving section 23, the received light signal (second signal) ⑦ obtained from the second light receiving section 35, or both the first signal and the second signal are used and whether measurements can be made is set by suitable factors.

The additional measurement section 280 makes, for example, a pulse measurement. By the additional measurement section 280, a measurement in view of the pulse can be made. The calculation section 210 receives a signal corresponding to the pulse of a person to be measured from the additional measurement section 280, and in response to the signal corresponding to the pulse, the subsequent measurement timing can be determined in substantially the same state as the pulse state at the point of time of the first measurement. The calculation section 210 further receives the signal corresponding to the pulse of the person to be measured from the additional measurement section 280, and in response to the signal corresponding to the pulse, the measurement timing can be determined when a predetermined pulse state occurs. As stated above, in the calculation section 210, for example, the measurement timing can be determined with the pulse.

Figure 16:
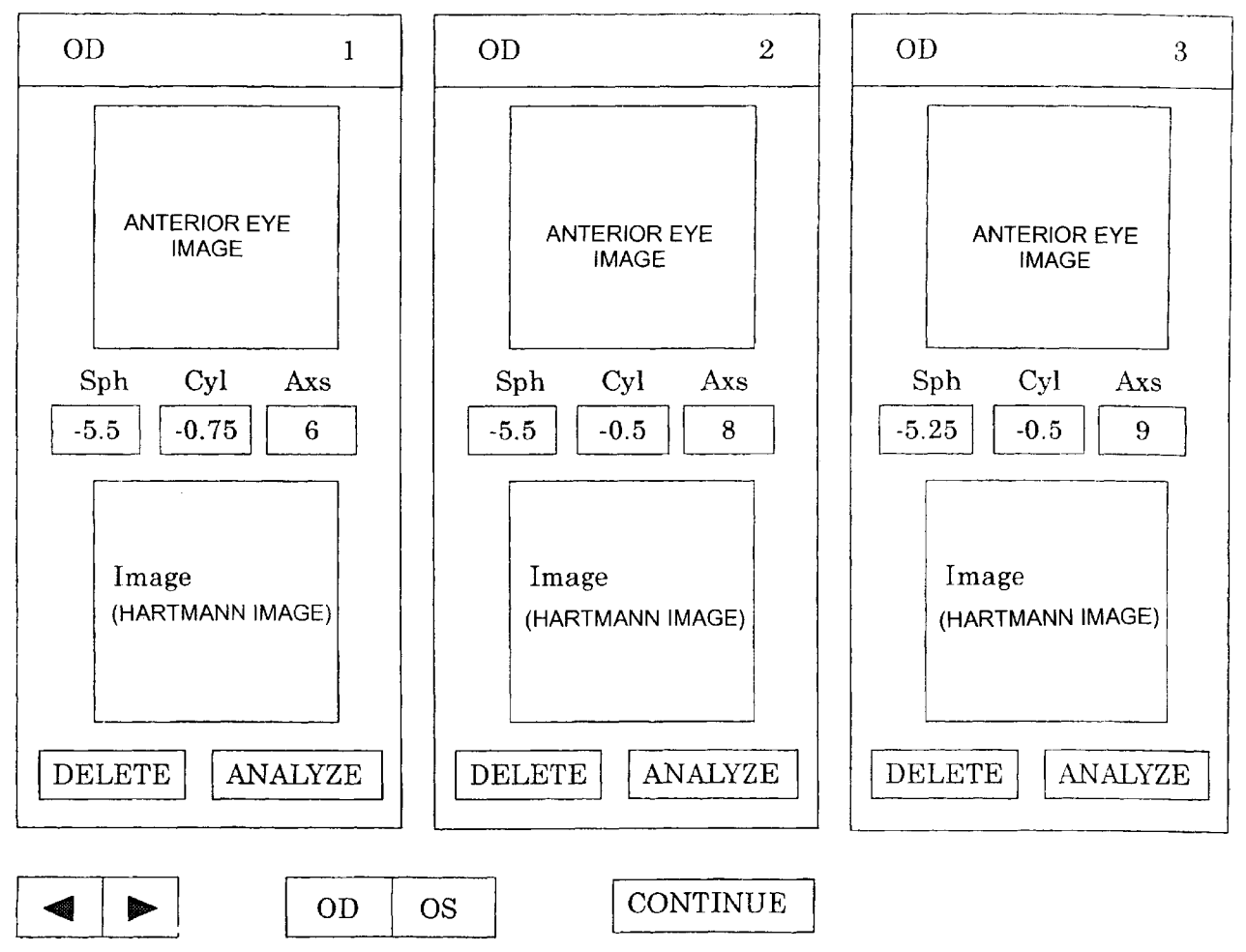

The display section 230 displays the first and/or the second signal from the first light receiving section 23 and/or the second light receiving section 35 as an image. FIG. 16 is an explanatory view of the image display. Here, the display section 230 displays the first and the second signals as images, however, one of the first signal and the second signal may be displayed as the image. This setting can be made in advance by the input section 270 or the like. On the basis of the image display of the first and/or the second signal displayed on the display section 230 by the input section 270, the first and the second signals used for the calculation processing are selected. From these images, the operator judges whether or not measurement adaptability is attained by the foregoing respective decision factors for measuring timing, and whether or not the signals are adapted as the measurement objects, and suitably selects a desired image.

In this drawing, the anterior eye part and the Hartmann image form a pair, and three pairs of images are displayed on one screen. In the respective screens, in the case of data for measuring the optical characteristics, [ANALYZE] is clicked, and in the case where it is desired to exclude them from measurement objects, [DELETE] is clicked to select an image. In the case where they are not selected, the pressing of [DELETE] can be omitted. Alternatively, in the case where they are selected, the pressing of [ANALYZE] may be omitted. When the selection of the displayed screen is completed, an arrow key at the lower left part is clicked to move the screen to a next screen or a former screen, and this is repeated until necessary selections are completed. [OD] denotes a right eye, and [OS] denotes a left eye. When [OD] is pressed, only images concerning the right eye are displayed, and when [OS] is pressed, only images concerning the left eye are displayed. When all selections are ended, [CONTINUE] is clicked, and analysis of the optical characteristics is started on the basis of the selected data. The analysis of the optical characteristics concerning the image may be performed when [ANALYZE] is clicked. Incidentally, for example, when a measurement is made at the same time as a refract meter, that is, in the case where refractive power of the subject eye, an astigmatism degree, and an astigmatism axis angle are known, those indications may be added to the center portion. In the case where these values are measured each time the Hartmann image is captured, by their dispersion, they can be made the basis of judgment as to whether selection is made. The analysis of the optical characteristics is not carried out, but only the acquired image may be stored. At this time, the analysis can be carried out later.

In the case where the display section 230 displays one of the first signal of the first light receiving section 23 and the second signal of the second light receiving section 35 as the image, when the input section 270 selects a signal used for the calculation processing from the image display of the one signal displayed on the display section 230, on the basis of the signal selected by the input section 270, the calculation section 210 uses the selected one signal and the other signal measured at the same timing or substantially the same timing as the first and the second signals to obtain the optical characteristics of the subject eye and the corneal shape of the subject eye. In the case where the display section 230 displays the first and the second signals of the first light receiving section 23 and the second light receiving section 35 as images, when the input section 270 selects the first and the second signals used for the calculation processing from the image display of the first and the second signals displayed on the display section 230, the calculation section 210 obtains the optical characteristics of the subject eye and the corneal shape of the subject eye on the basis of the first and the second signals selected by the input section 270.

The calculation section 210 may be structured such that the first and the second signals of the first light receiving section 23 and the second light receiving section 35 are subjected to a judgment processing for judging whether or not they are data suitable for the processing in the calculation section 210, and at this time, the display section 230 is structured to display the judgment processing result of the calculation section 210, and the input section 270 is structured to select the first and the second measurement signals used for the measurement calculation processing on the basis of the judgment processing result displayed on the display section 230.

Figure 4:
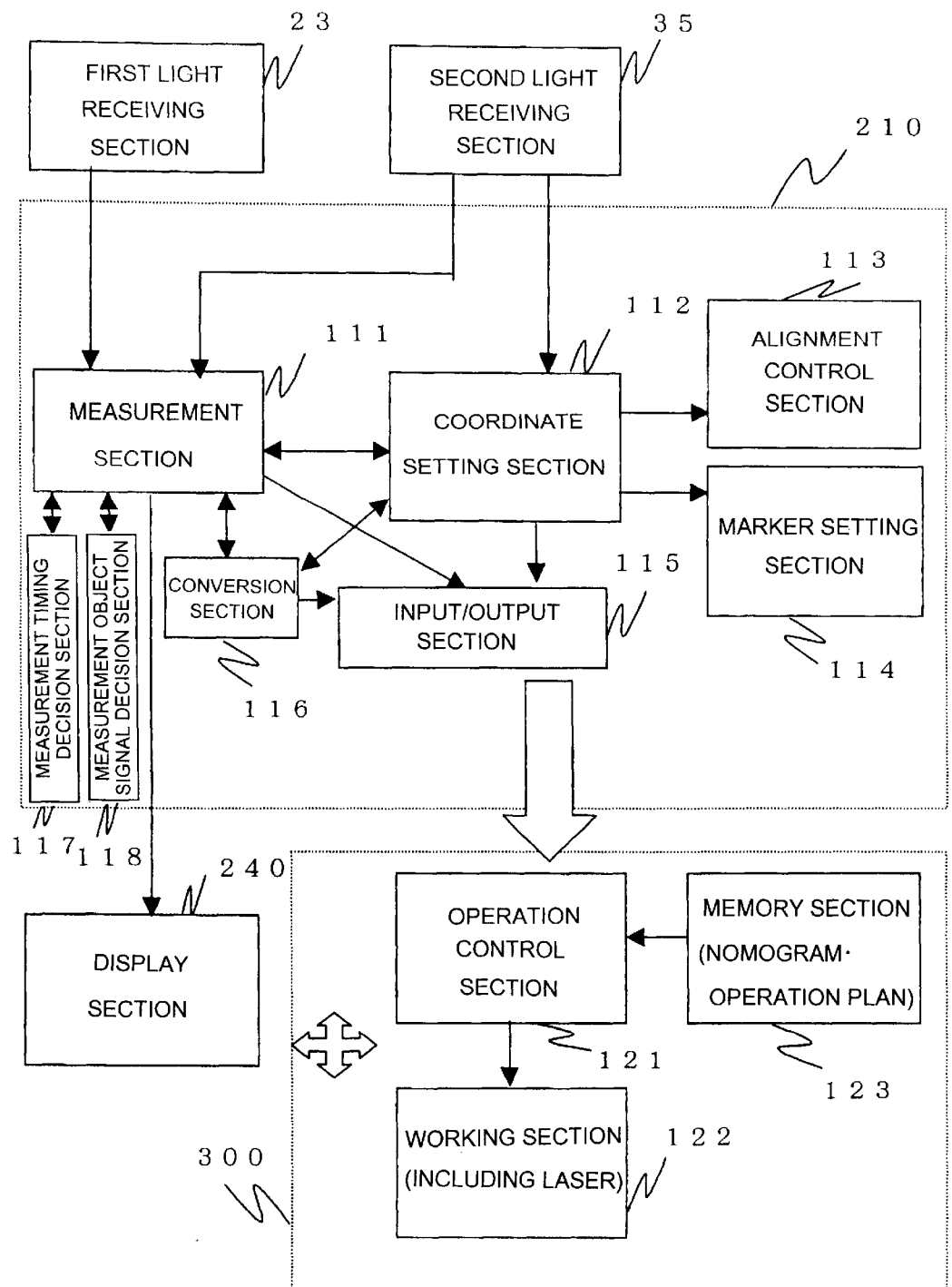
FIG. 4 is a detailed structural view of a calculation section of the ophthalmic characteristic measuring apparatus of the invention.

FIG. 4 is a detailed structural view of the calculation section of the ophthalmic characteristic measuring apparatus of the invention. The calculation section 210 includes a measurement section 111, a coordinate setting section 112, an alignment control section 113, a marker setting section 114, an input/output section 115, a conversion section 116, a measurement timing decision section 117, a measurement object signal decision section 118, and a sight line detection section 119. Incidentally, either one of the measurement timing decision section 117 and the measurement object signal decision section 118 may be provided. The sight line detection section 119 may be omitted.

The first light receiving section 23 forms a first received light signal from the received light flux reflected and returned from the eyeground of the subject eye. The second light receiving section 35 forms a second received light signal including information of the anterior eye part from the received light flux including the feature portion of the anterior eye part of the subject eye and/or information relating to the marker formed in the anterior eye part of the subject eye, and guides it to the measurement section 111 and the coordinate setting section 112.

The measurement section 111 obtains the refractivity of the subject eye or the optical characteristics including the corneal shape on the basis of the first received light signal from the first light receiving section 23. The measurement section 111 makes a measurement of ophthalmic optical characteristics especially on the basis of the first received light signal from the first light receiving section 23. Besides, the measurement section 111 makes a corneal shape measurement such as a cornea topography measurement especially on the basis of the second received light signal from the second light receiving section 35. The measurement section 111 calculates an aberration result, and if necessary, an aberration amount, and outputs the calculation result through the input/output section 115 to an operating apparatus. The measurement section 111 obtains the optical characteristics of the subject eye on the basis of the first signals captured plural times, and obtains the corneal shape of the subject eye on the basis of the second signals from the second light receiving section, which are captured plural times at the same timing or substantially the same timing.

The measurement section 111 captures the first and the second signals from the first light receiving section 23 and the second light receiving section 35 at the same timing or substantially the same timing, obtains the optical characteristics of the subject eye on the basis of the first signal from the first light receiving section 23, and obtains the corneal shape of the subject eye on the basis of the second signal from the second light receiving section 35.

The coordinate setting section 112 converts signals of the first and the second coordinate systems corresponding to the pupil of the subject eye included in the first and the second received light signals into signals of the reference coordinate system. The coordinate setting section 112 obtains a pupil edge and a pupil center on the basis of the respective signals of the first and the second coordinate systems.

Besides, the coordinate setting section 112 decides the coordinate origin and the direction of the coordinate axis on the basis of the second received light signal including the feature signal of the anterior eye part of the subject eye. Besides, the coordinate setting section 112 obtains the coordinate origin, and the rotation and movement of the coordinate axis on the basis of at least one of the feature signals of the anterior eye part of the subject eye in the second received light signal, and correlates the measurement data with the coordinate axis. Incidentally, the feature part includes at least one of pupil position, pupil center, vertex normal, iris position, iris pattern, shape of the pupil, and limbus shape. For example, the coordinate setting section 112 sets the coordinate origin of the pupil center, the vertex normal or the like. The coordinate setting section 112 forms the coordinate system on the basis of the feature signals corresponding to the image of the feature portion of the anterior eye part of the subject eye included in the second received light signal. Besides, the coordinate setting section 112 forms a coordinate system on the basis of the marker signal concerning the marker provided at the subject eye included in the second received light signal and the signal concerning the anterior eye part of the subject eye. The coordinate setting section 112 can determine the coordinate origin and the direction of the coordinate axis on the basis of the second received light signal including the marker signal. The coordinate setting section 112 obtains the coordinate origin on the basis of the marker signal in the second received light signal, obtains the rotation and movement of the coordinate axis on the basis of at least one of the feature signals of the anterior eye part of the subject eye in the second received light signal, and can correlates the measurement data with the coordinate axis. Alternatively, the coordinate setting section 112 obtains the coordinate origin on the basis of at least one of the feature signals concerning the anterior eye part in the second received light signal, obtains the rotation and movement of the coordinate axis on the basis of the marker signal in the second received light signal, and correlates the measurement data with the coordinate axis. Alternatively, the coordinate setting section 112 obtains the coordinate origin, the rotation and movement of the coordinate axis on the basis of at least one of the feature signals of the anterior eye part of the subject eye in the second received light signal, and correlate the measurement data with the coordinate axis.

The conversion section 116 correlates the first and second optical characteristics of the subject eye obtained by the measurement section 111 with the respective reference coordinate systems formed by the coordinate setting section and synthesizes them. The conversion section 116 makes conversion into the reference coordinate system by making the pupil center obtained by the coordinate setting section 112 the origin.

One of, some of, or all of the first illumination optical system 10, the first light receiving optical system 20, the second light receiving optical system 30, the common optical system 40, the adjusting optical system 50, the second illumination optical system 70, and the second light sending optical system 80 are suitably put on the alignment section of the optical system 100. The alignment control section 113 can move the alignment section in response to the movement of the subject eye in accordance with the calculation result of the coordinate setting section 112 on the basis of the second received light signal obtained by the second light receiving section. The marker setting section 114 forms the marker related to this coordinate system in the anterior eye part of the subject eye on the basis of the coordinate system set by the coordinate setting section 112. The input/output section 115 is an interface for outputting data and calculation results such as aberration amount, coordinate origin, coordinate axis, rotation of coordinate axis, and movement thereof, to an operating apparatus. The display section 240 displays the optical characteristics of the subject eye obtained by the measurement section 111 in relation to the coordinate system formed by the coordinate setting section.

An operating apparatus 300 includes an operation control section 121, a working section 122, and a memory section 123. The operation control section 121 controls the working section 122, and controls an operation such as keratectomy. The working section 122 includes a laser for the operation such as keratectomy. The operation memory section 123 stores data for keratectomy, nomogram, and data for operations such as operation plans.

The measurement timing decision section 117 decides measurement timing of the first signal and the second signal as the objects of measurement calculation on the basis of the first and/or the second signal. The measurement timing decision section 117 uses, as a predetermined decision factor for measuring timing, at least one of a blink, a poor tear film, a lack of a pupil diameter, and a poor opening eyelid. The measurement timing decision section 117 judges the suitableness of the measurement with the first decision factor for measuring timing on the basis of the first signal, and judges the suitableness of the measurement with the second decision factor for measuring timing on the basis of the second signal, and in accordance with the judgment, the measurement timings of the first signal and the second signal are decided. The first decision factor for measuring timing is at least one of a blink, a poor tear film, a lack of a pupil diameter, and a poor opening eyelid, and the second decision factor for measuring timing is at least one of a blink, a poor tear film, a lack of a pupil diameter, a poor opening eyelid, and a fixation disparity. The measurement timing decision section 117 detects the blink on the basis of the first signal and/or the second signal, sets predetermined measurable range on the basis of the timing of the blink, and further determines the measurement timing of the first signal and the second signal on the basis of the suitableness of the measurement with the decision factor for measuring timing of the first signal or the second signal. At this time, as the decision factor for measuring timing of the first signal or the second signal, at least one of pupil diameter, state of tear film, and opening degree of eyelid can be selectively set. Further, the measurement timing decision section 117 determines the measurement timing of the first signal and the second signal at the same timing or substantially the same timing. When the measurement adaptable conditions of the first signal and the second signal are satisfied, the measurement timing decision section 117 causes the measurement section 111 to automatically start the measurement or permits the measurement.

The measurement object signal decision section 118 decides the first signal and the second signal as the objects of measurement calculation. The measurement object signal decision section 118 judges the suitableness of measurement with the predetermined decision factor for measuring timing on the basis of the first signal and/or the second signal, and decides the measurement object signal of the first signal and the second signal in response to this. The predetermined measurement object signal decision factor can be made one of a blink, a lack of a pupil diameter, and a poor opening eyelid. The measurement object signal decision section 118 judges the suitableness of measurement with the first decision factor for measuring timing on the basis of the first signal, judges the suitableness of measurement with the second decision factor for measuring timing on the basis of the second signal, and determines the measurement timings of the first signal and the second signal in accordance with the judgments. At this time, the first decision factor for measuring timing is made at least one of a blink, a poor tear film, a lack of a pupil diameter, and a poor opening eyelid, and the second decision factor for measuring timing is made a blink, a poor tear film, a lack of a pupil diameter, a poor opening eyelid, and a fixation disparity.

The sight line detection section 119 detects the direction of the sight line of the subject eye on the basis of the third illumination optical system for illuminating the cornea of the subject eye with parallel light flux and the position of illumination light by the third illumination optical system from the second light receiving section 35. The sight line detection section 119 is further provided, and the measurement section 111 of the calculation section 210 may suppress the measurement when the fixation disparity is detected by the sight line detection section.

Here, the decision factor for measuring timing detected by the first signal and the second signal will be described. Here, among various calculations performed by the calculation section 210, a measurement calculation relating to the first signal and the second signal will be mainly described.

FIG. 5 is an explanatory view of the decision factor for measuring timing relating to the first signal and the second signal.

A table 271 is a table showing the decision factor for measuring timing detected with the first signal and the second signal, and the decision factor for measuring timing includes, for example, a blink, a tear film, a pupil diameter, an opening eyelid, and fixation state. With respect to the fixation state, according to whether the pupil center is within a predetermined distance from the vertex or is largely deviated, it is possible to judge adaptability as to whether measurements can be made. In the drawing, a mark of '⊙', a mark of 'O', a mark of 'Δ', and a mark of 'X' given correspondingly to the respective decision factors for measuring timing of the first signal and the second signal denote measurement good, measurable, measurement difficult, and measurement impossible, respectively.

A table 272 is a table showing adaptable conditions suitable for measurement in the case where the same decision factor for measuring timing is detected with different signals, that is, the first and the second signals, and the decision factor for measuring timing includes, similarly to the table 271, a blink, a tear film, a pupil diameter, an opening eyelid, and a fixation state. Here, as adaptable conditions, the fixation state is not suitable (−), and the others are good ('⊙'). A table 273 is a table showing adaptable conditions in the case where different decision factors for measuring timing or the same decision factor for measuring timing is detected with different signals, and as the respective decision factors for measuring timing, internal aberration detected only with the first signal is added as the decision factor, and adaptable conditions are indicated by the combination of these decision factors for measuring timing. In the case where the same decision factor for measuring timing (blink, tear film, pupil diameter, opening eyelid, etc.) is detected with the first and the second signals, the adaptable condition becomes good ('⊙'). In the case where different decision factors for measuring timing are detected with the first and the second signals, it becomes usable ('O') as an a adaptable condition by the illustrated combination. Incidentally, here, since it is supposed that the fixation state can not be measured with the first signal with accuracy, it is not adaptable to conditions that the fixation state with the first signal is used as the decision factor for measuring timing (−).

Here, the judgment of the suitableness of measurement with the decision factor for measuring timing of the first signal will be described while the calculation section 210 is correlated with the respective decision factors for measuring timing shown in the tables 271 to 273. Incidentally, the input section 230 can suitably select the case where the decision factor for measuring timing of the first signal is set and the case where it is not set. The calculation section 210 counts, on the basis of the first signal, how many region points received by the first light receiving section 23 exceed a predetermined level, or how many peak levels of signals received by the first light receiving section 23 exceed a predetermined value. By this, the calculation section 210 can judge whether data sufficient to finally obtain measurement results can be acquired. The calculation section 210 can judge the suitableness of measurement as described below (see the tables 271 to 273).

By detecting whether the first signal level is instantaneously wholly lowered, it is judged that there has occurred a blink.

By detecting whether a part of the periphery of the first signal level is lowered, it is judged whether or not the opening degree of an eyelid is sufficient.

By detecting whether the first signal level fluctuates, it is judged whether or not the tear film is unstable.

By detecting whether the first signal level is lowered at the periphery, it is judged whether or not the pupil diameter is decreased. Incidentally, in the ophthalmic characteristic measuring apparatus of the invention, with respect to the miosis, since the light flux of near infrared is used as the light source, it is not dazzling and the miosis does not occur, so that continuous measurement can be made.

Next, the judgment of suitableness with the decision factor for measuring timing of the second signal will be described while the calculation section 210 is correlated with the respective decision factors for measuring timing shown in the tables 271 to 273. Incidentally, the input section 230 can select, on the basis of the second signal, for example, the decision factor for measuring timing with a combination of one or plural factors. The decision factor for measuring timing of the second signal by the calculation section 210 includes blink, pupil diameter, state of tear film, and opening degree of eyelid. The calculation section 210 can judge the suitableness of measurement as described below (see the tables 271 to 273).

With respect to the blink, the blink is detected and immediately after that, a measurement can be made under fixation. As the kind of the blink, for example, the eyelids are closed for several seconds and are opened, the eyelids are tightly closed, or the eyelids are normally softly closed continuously several times. As measurement intervals, for example, immediately after the blink, or after fixed seconds based on the past suitable measurable empirical value, a measurement is made. Incidentally, as the suitable measurable empirical value, for example, the measurement value and analysis result by a skilled person are made to correspond to intervals to obtain a specified value for each patient, and it is expected that more accurate measurement result is obtained. Further, for example, the miosis temporarily occurs just after the blink, however, the pupil is widened at once and becomes slightly stable, and a period after several ms when the tear film also becomes stable is suitable for measurement, and the calculation section 210 can calculate image data of the anterior eye part with high accuracy by using this timing.

By detecting whether or not the pupil is larger than a predetermined diameter (for example, 6φ in dark field), it is judged whether the pupil diameter is suitable.

By detecting distortion of the pattern 275 with the placido's disc 71, whether the co-axial rings are not continuous, or whether fluid distortion occurs, it is judged whether the tear film is suitable.

By detecting whether the ratio of the limbus diameter to the eyelid interval is a predetermined value or more, it is judged whether the opening degree of the eyelid is suitable.

In this embodiment, the operator can visually examine whether the first signal and the second signal as set forth above are adaptable to measurement. Qualitatively speaking, for example, it is possible to confirm that an eyelid is covered, a ring is cut, a ring is blurred, contrast is poor, etc.

FIG. 6 is an explanatory view of an image received by the first and the second light receiving sections.

A Hartmann image 274 received by the first light receiving section is, for example, an image on the basis of the reflected light from the eye 60 to be measured, and includes plural region points (in the drawing, circles, ellipses, etc.) in the case where the reflected light as the light flux roughly spread outward through the Hartmann plate 22 is received by the first light receiving section 23. For example, at portions where the tear film of the eye 60 to be measured is broken, or thin, or thick, the plural region points included in the Hartmann image 274 in this example have elliptical states or states where the region points themselves are not seen, that is, the arrangement of the plural region points is in an irregular state. A light signal relating to the Hartmann image 274 is converted into an electric signal, and is inputted (or captured) as the first signal into the calculation section 210.

In a placido's disc image 275 received by the second light receiving section, at the portion where the tear film of the eye 60 to be measured is broken, thin or thick, rings of the co-axial rings included in the image are discontinuously observed. An optical signal relating to the placido's disc image 275 is converted into the electric signal and is inputted (or captured) as the second signal into the calculation section 210.

Next, the operation of the ophthalmic characteristic measuring apparatus of the invention will be described using a time chart and a flowchart.

The calculation section 210 obtains the optical characteristics of the subject eye and the corneal shape of the subject eye on the basis of the first and the second signals selected by the input section 270. In the calculation section 210, by the number (one or plural) of the decision factors for measuring timing relating to the decision of measurement timing, and the combination of the first signal and the second signal (the first and/or the second signal, the first and the second signals, only the first signal), plural calculation patterns are executed (see four flowcharts described later). Specifically, the calculation section 210 captures, for example, the signals of the first signal and the second signal plural times and makes measurements. Besides, the calculation section 210 includes, for example, the measurement timing decision section 117 for deciding the measurement timing, or the measurement object signal decision section 118, or both the decision sections, and by this, the calculation section judges, on the basis of the first and/or the second signal, the suitableness of measurement with the factor for determining a predetermined measurement timing, and on the basis of this judgment, the measurement timings of the first signal and the second signal are determined or the measurement object signal is selected.

Hereinafter, respective embodiments will be described.

(1) First Embodiment

Figure 7:
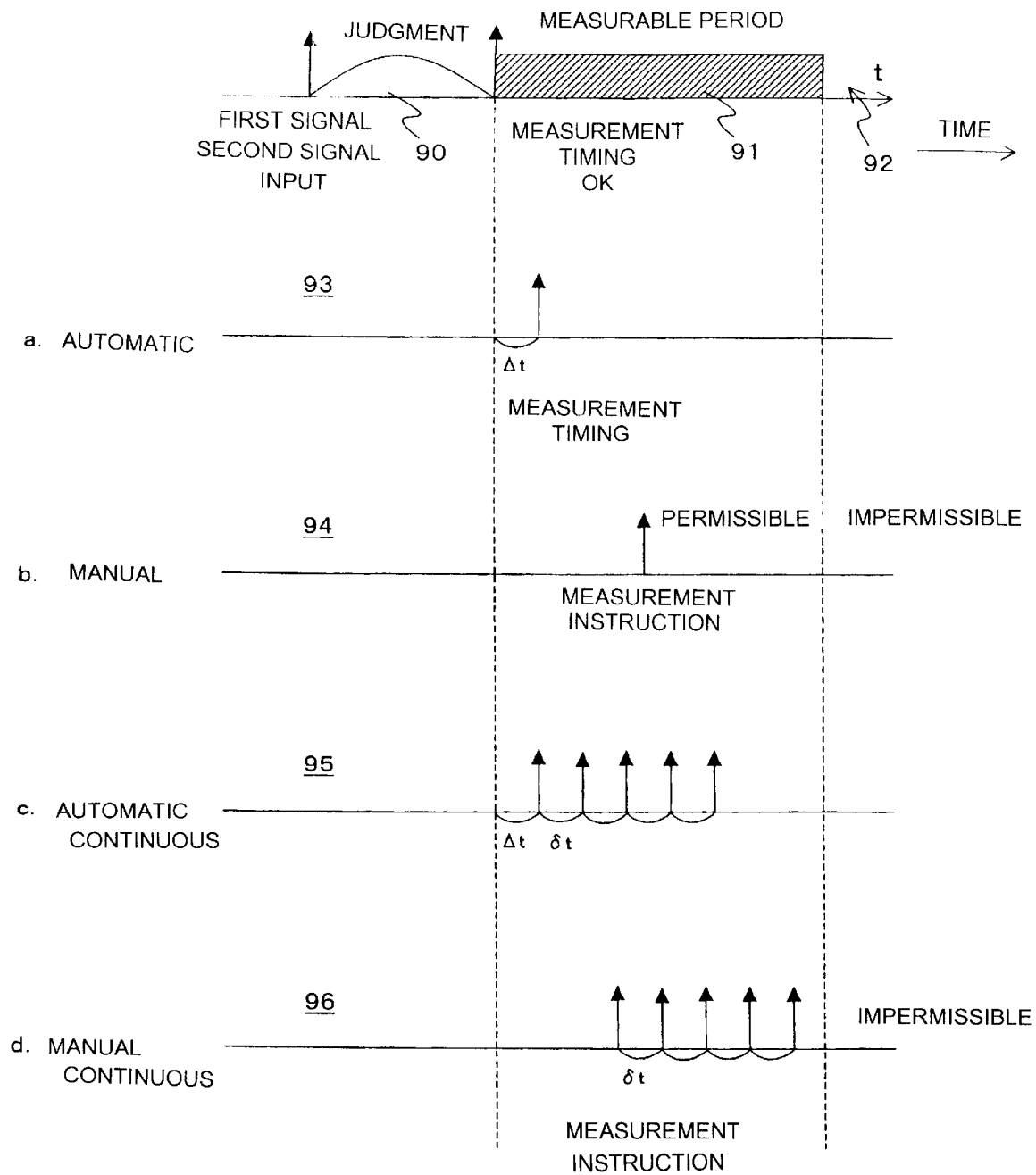
FIG. 7 is an explanatory view of a first embodiment relating to ophthalmic characteristic measurement.

FIG. 7 is an explanatory view of a first embodiment relating to ophthalmic characteristic measurement.

This first embodiment shows the operation of the case where decision factors for measuring timing are checked by, for example, the first signal and/or the second signal to determine the measurement timing.

As the measurement mode, by combination of, for example, automatic or manual, and single or continuous, an automatic (single) mode 93, a manual (single) mode 94, an automatic continuous mode 95, and a manual continuous mode 96 can be respectively selected by the input section 270. First, the outline of decision of measurement timing in the respective measurement modes will be described along a time axis. For example, the measurement timing decision section 117 of the calculation section 210 receives the first signal, the second signal, or both the signals and judges whether a measurement can be made (measurement judgment period 90). When it is judged that the measurement can be made, a predetermined measurable period 91 is set. The length of the measurable period 91 is determined in advance by the input section 270 or the like. After the measurable period 91 has passed, a measurement impossible period 92 comes. Incidentally, the measurement timing decision section 117 judges whether the measurement can be made, by measurement conditions on the basis of the decision factor for measuring timing of the first signal, the second signal, or both the first signal and the second signal.

The automatic mode 93 is a mode in which for example, a measurement is automatically started at the timing when all the set measurement conditions are satisfied, and when the measurable period 91 comes, the measurement is made immediately or after Δt. Incidentally, the value of Δt can be suitably set by the input section 270 or the like. The manual mode 94 is determined as a measurement waiting period for a predetermined time since all the set measurement conditions were satisfied, and the measurable period 91 is displayed to the operator with a suitable display of the display section 230. Incidentally, as the display section, for example, a display lamp, a finder switch or the like may be attached to the input section 270. In this measurable period 91, the operator gives measurement instructions using the finder or the like of the input section 270, and the first and the second signals are measured by the calculation section 210. Although the measurement instructions are permitted in the measurable period 91, they are not permitted in the measurement impossible period 92. Incidentally, in the measurable period 91, measurements can be made plural times by the instructions of the operator.

The automatic continuous mode 95 is a mode in which for example, in a period when the set measurement conditions are satisfied, when the measurable period 91 comes, a measurement is made immediately or after Δt, and further, measurements are continuously made a predetermined number of times (or a predetermined interval δt) determined by the input section 270 or the like in advance. Incidentally, the value of δt can be suitably set by the input section 270 or the like.

In the manual continuous mode 96, for example, since all the set decision factors for measuring timing were satisfied, the setting possible period (here, measurement waiting state) 91 comes, and measurements are made by measurement instructions from the operator in the measurable period 91, and the measurements are continuously made a predetermined number of times at a predetermined interval δt from the measurement instructions. Incidentally, the value of δt can be suitably set in advance by the input section 270 or the like. With respect to the measurement instructions, the measurement is permitted in the case where the final measurement timing is in the measurable period 91, and the measurement is not permitted in the case where it is in the measurement impossible period 92.

Figure 8:
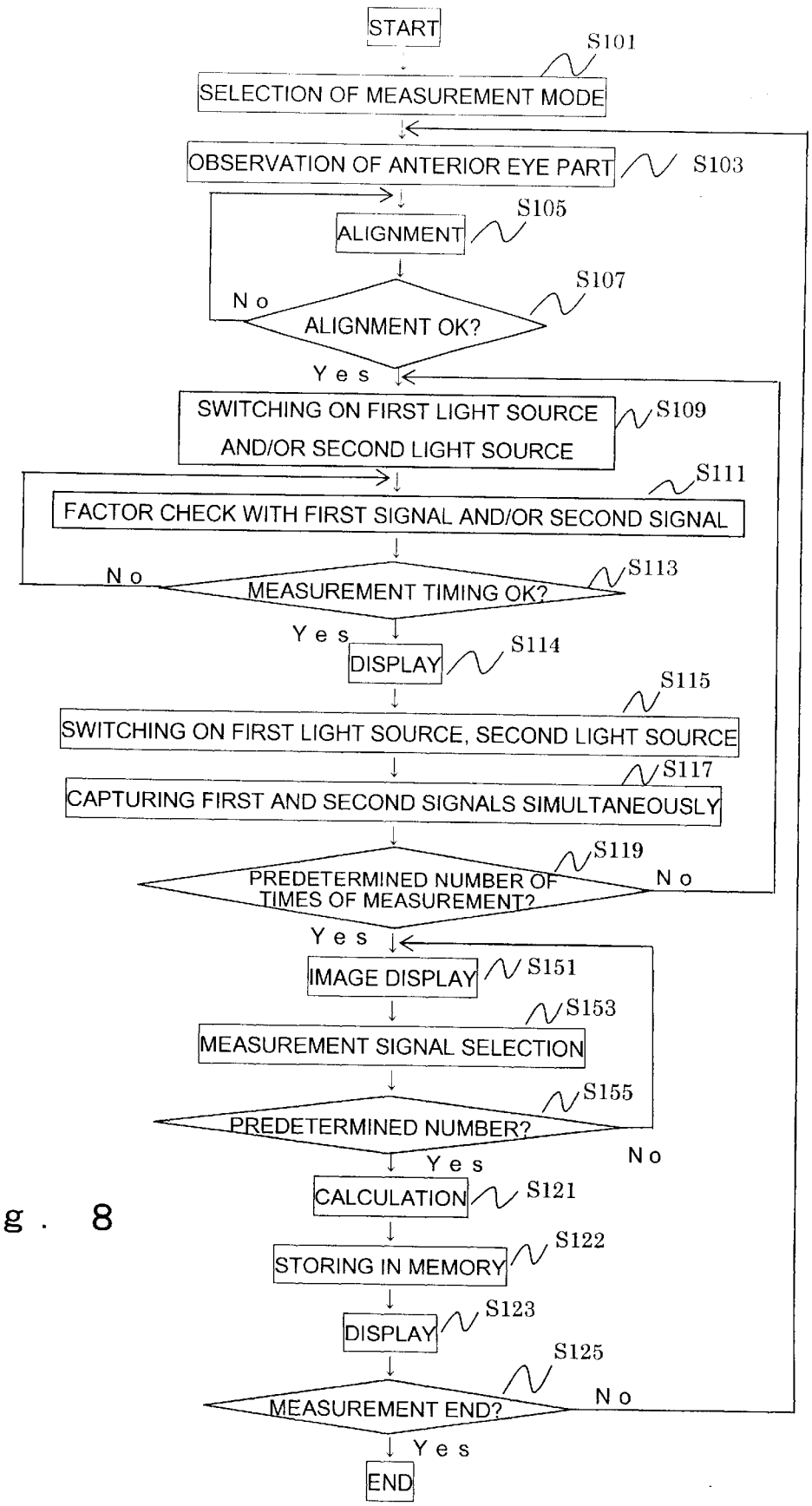
FIG. 8 is a flowchart of the first embodiment showing the operation of the ophthalmic optical characteristic measuring apparatus of the invention.

FIG. 8 is a flowchart of the first embodiment showing the operation of the ophthalmic optical characteristic measuring apparatus of the invention.

First, a measurer (operator) starts a measurement of the eye 60 to be measured as the measurement object, and the measurement mode (one of the automatic mode 93, the manual mode 94, the automatic continuous mode 95, and the manual continuous mode 96) is selected by the input section 270 (S101).

The signal from the second light receiving section 35 is formed as an anterior eye image on a monitor screen of the display section 230 (S103). Next, reflected light of the cornea vertex is used as an alignment target, and alignment is performed in the horizontal direction (optical axis of the cornea vertex and the apparatus, XY direction), and alignment in the vertical direction (depth direction, Z direction) is performed by a Z alignment apparatus (S105). The optical characteristic measuring apparatus 100 judges whether the alignment is completed (S107). In case the alignment adjustment is insufficient, the procedure is again returned to the step S105, and the alignment adjustment is performed.

Next, in accordance with the decision factor for measuring timing set by the input section 270, the optical characteristic measuring apparatus 100 switches on the first light source and/or the second light source (S109). The measurement timing decision section 117 of the calculation section 210 judges, in accordance with the decision factor for measuring timing, whether the measurable period 91 as a period of measurement timing can be set (S113) When the measurement timing decision section 117 judges, in accordance with the decision condition corresponding to the respective decision factors for measuring timing, that a measurement can be made, the calculation section 210 makes, in the setting possible period, the setting possible period 91 visible or audible by, for example, a lamp or a speaker included in the display section 230 or the input section 270 (S114). Incidentally, at the time of the automatic mode (single, continuous), the step S114 can be omitted.

Next, in accordance with the mode selected in the measurable period, the optical characteristic measuring apparatus 100 switches on the first light source and the second light source (S115). The calculation section 210, for example, captures the first and the second signals simultaneously or substantially simultaneously (S117). In the first measurement system, at the step S103, the first received light signal concerning the Hartmann image is captured using the first light receiving section 23 of a low noise CCD or the like. On the other hand, in the second measurement system, as shown in step S191, substantially at the same time as capturing of the first received light signal, capturing of the second received light signal concerning the anterior eye image is also performed by the second light receiving section 35. As described above, measurements are made, in the automatic mode 93, immediately after the start timing of the measurable period 91 or after Δt, in the manual mode 94, at the time of measurement instructions through the finder of the input section 270 in the measurable period 91, in the automatic continuous mode 95, immediately after the start timing of the measurable period 91 or after Δt, plural times at predetermined intervals (δt), and in the manual continuous mode 96, after the measurement instruction in the measurable period 91 plural times at predetermined intervals (δt).

Next, the calculation section 210 judges whether measurements are made the predetermined number of times or more in order to acquire the first and the second signals sufficient for the measurement (S119). In the case where measurements are not made the predetermined number of times or more at the step S119, the calculation section 210 again returns to the step S109. On the other hand, in the case where measurements are made the predetermined number of times or more at the step S119, the calculation section 210 reads out a predetermined number of the first and the second signals from the memory 240, and carries out an image display on the display section 230 (S151). At this time, as described above, the image to be displayed may be the image of either one of the first signal and the second signal, or the images of both the signals. Besides, each time a measurement is made once, an image display may be carried out. Besides, a display can be carried out over plural pages or plural screens. Further, at this time, the display section 230 may be constructed such that it displays a judgment processing result as to whether or not the image of the calculation section 210 is suitable, so that the operator can refer to it. Next, when the operator confirms the displayed image to select signals to be used as the measurement object by the input section 270, the calculation section 210 selects the first signal and the second signal corresponding to the selected signal as the first and the second measurement signal used for the subsequent calculation from the memory 240, and if necessary, stores them in the memory 240 (S153). When signals are not selected by the predetermined number (for example, three or four, etc.) determined by the input section 27 or the like, the calculation section 210 returns to the step S151, and again carries out an image display (S135). On the other hand, when the predetermined number of the first and the second measurement signals are selected, the processing proceeds to a subsequent calculation processing.

The measurement section 111 obtains the optical characteristics on the basis of the selected first or second measurement signal (S121). Here, the optical characteristics include, for example, aberration (cornea, internal, eye), refractivity, corneal shape, and the like. That is, at the step S121, the calculation section 210 calculates the optical characteristics by the measurement principle of a Hartmann wavefront sensor with respect to the first measurement system. The wavefront aberration (ocular higher order aberration) of an eyeball optical system is obtained by this (see FIG. 9A). Besides, with respect to the second measurement system, since the tilt of the cornea is obtained, by the calculation section 210, the height of the cornea is calculated from this, and the cornea is treated similarly to an optical lens (mirror surface), so that the optical characteristics are calculated. The wavefront aberration (corneal higher order aberration) generated on the cornea front surface is obtained here (see FIG. 9B). Incidentally, each time a signal to be used is selected, the optical characteristics may be obtained on the basis of the signal.

Next, the measurement section 111 of the calculation section 210 calculates output data, and stores the measurement result at the step S121 in the memory 240 (S122). As the output data, for example, data of the reference coordinate system, measurement data, aberration amount itself of the subject eye, optical characteristic data, aberration amount required for erasion by an operating apparatus, and the like are obtained through calculation.

Next, the calculation section 210 displays the measurement result and output data stored in the memory 240 at the step S122 on the display section 230 (S123). Incidentally, at the step S123, in the case where the plural first and second signals are selected, the images or data concerning the obtained plural ophthalmic characteristics may be displayed, or images or data in which statistical processing such as averaging may be displayed. With respect to the display of the optical characteristics by the display section 240, for example, as shown in FIG. 9, ocular higher order aberration map relating to the first measurement system and corneal higher order aberration map relating to the second measurement system are separately displayed, and at the same time, (differential higher order aberration map)=(ocular higher order aberration map)−(corneal higher order aberration map) is also displayed (see FIG. 9C). This differential higher order aberration map optically indicates the influence on the aberration of internal optical system except for the cornea front surface of the eyeball optical system, and is a map very useful for diagnosis of such disease that abnormality occurs in refractive index distribution of a crystalline lens, for example, cataract.

Further, if necessary, these output data can be outputted. Here, as output modes, for example, there are following modes.

<1> A mode is offline and data is outputted by a recording medium such as a floppy disk or a CD-ROM, or an interface such as a signal line, wireless line, and then, an operation is performed in a different period.

<2> Output data is connected to the operation apparatus 300 online through an interface such as a signal line, and at an operation, the optical characteristics of the subject eye is measured continuously or by switching.

As described above, after the output of data, if measurement is not completed, it is repeated, and if completed, the measurement is ended (S125).

(2) Second Embodiment

Figure 10:
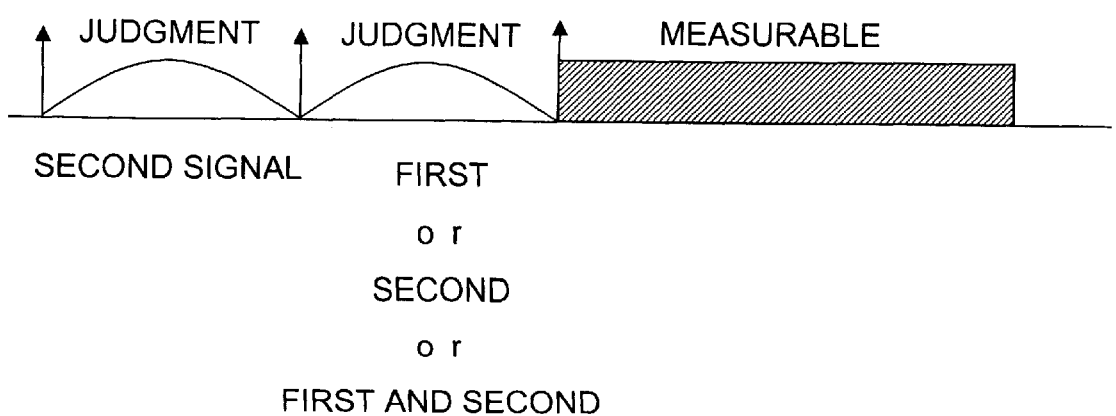
FIG. 10 is an explanatory view of a second embodiment relating to ophthalmic characteristic measurement.

FIG. 10 is an explanatory view of a second embodiment relating to ophthalmic characteristic measurement.

In the second embodiment, the measurement timing decision section 117 makes a first judgment with the second signal as to whether a measurement can be made in accordance with the first decision factor for measuring timing, and after the judgment that the measurement can be made, further makes a second judgment with the first signal and/or the second signal as to whether a measurement can be made in accordance with the second decision factor for measuring timing. When it is judged that the measurement can be made by the plural decision factors for measuring timing, the measurable range 91 is set, and the first and the second signals are captured. Incidentally, the first judgment by the first decision factor for measuring timing may be made with the first signal or both the first and the second signals.

Figure 11:
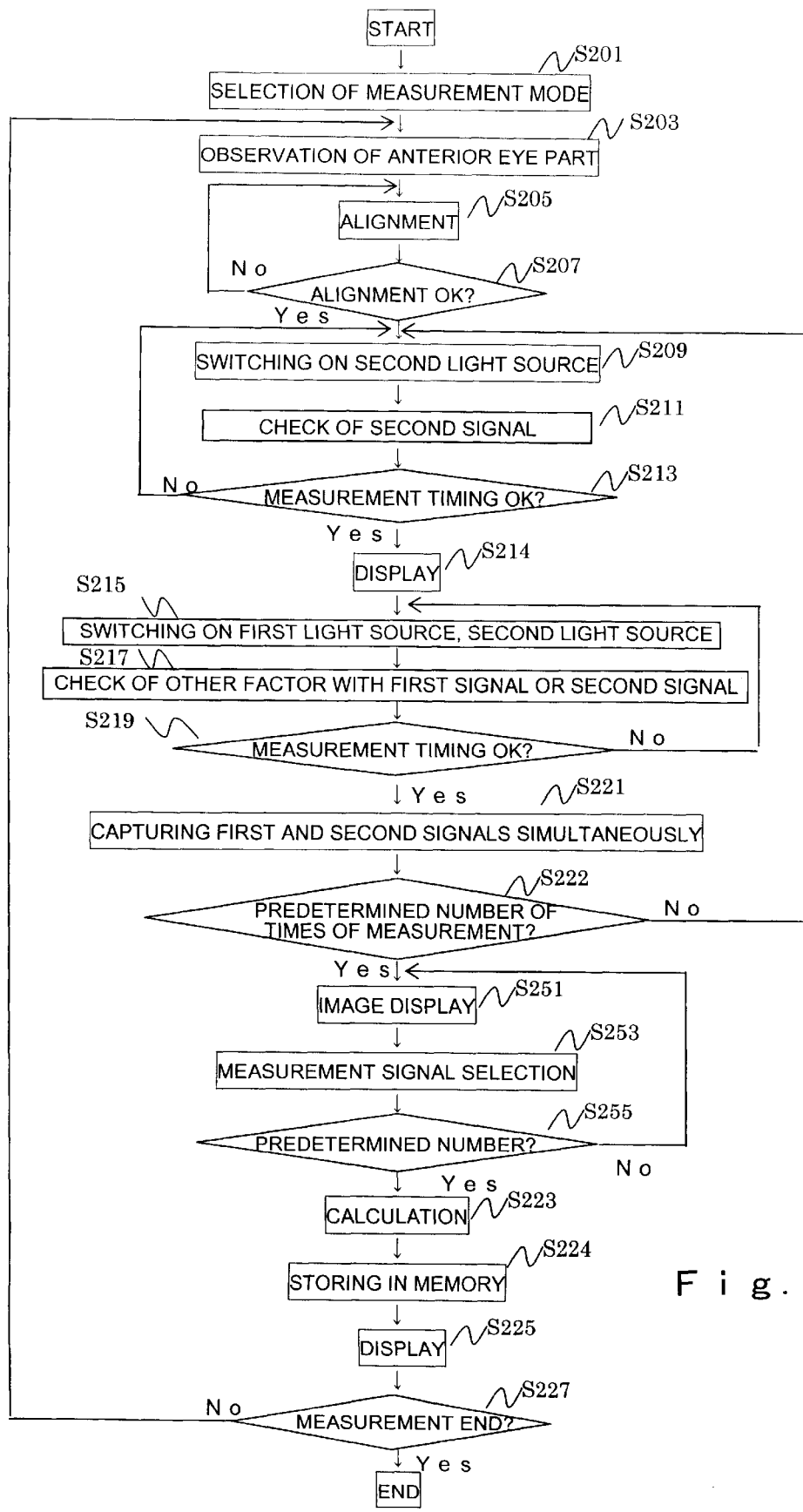
FIG. 11 is a flowchart of the second embodiment showing the operation of the ophthalmic optical characteristic measuring apparatus of the invention.

FIG. 11 is a flowchart of the second embodiment showing the operation of the ophthalmic optical characteristic measuring apparatus of the invention.

First, similarly to the first embodiment, the respective processings of selection of a measurement mode (S201), measurement of an anterior eye image (S203), and alignment (S205, S207) are carried out.

Next, the optical ophthalmic characteristic measuring apparatus 100 switches on the second light source (S209) in accordance with the first decision factor of measuring timing set by the input section 270. The measurement timing decision section 117 of the calculation section 210 judges whether or not the measurable period 91 as a period of measurement timing can be set in accordance with the first decision factor for measuring timing (S213). When the measurement timing decision section 117 judges that the measurement can be made in accordance with the decision condition corresponding to the respective decision factors for measuring timing, that measurement can be made is displayed visibly or audibly by a lamp of the display section 230 or a speaker (S214).

Next, the optical characteristic measuring apparatus 100 switches on the first light source and/or the second light source in accordance with the second decision factor for measuring timing set by the input section 270 (S215). The measurement timing decision section 117 of the calculation section 210 judges whether or not the measurable period 91 as the period of measurement timing can be set in accordance with the second decision factor for measuring timing (S217). When the measurement timing decision section 117 judges that the measurement can be made in accordance with the decision condition corresponding to the respective decision factors for measuring timing (S219), the measurements of the first and the second signals are made in the respective modes selected at the step S101. In the case where the measurable period 91 can not be set at the step S219, the procedure is again returned to the step S215.

Next, similarly to the first embodiment, the calculation section 210 captures the first and the second signals simultaneously or substantially simultaneously in accordance with the set mode (S221). Next, the calculation section 210 judges whether the measurement is made a predetermined number of times or more to acquire the first and the second signals sufficient for the measurement (S222). In the case where the measurement is not made the predetermined number of times at the step S226, the calculation section 210 again returns to the step S209. On the other hand, in the case where the measurement is made the predetermined number of times or more at the step S222, the calculation section 210 reads out the predetermined number of the first and the second signals from the memory 240, and carries out an image display on the display section 230 (S251). At this time, as described above, the image to be displayed may be an image of either one of the first signal and the second signal, or an image of both the signals. Each time the measurement is made, the image display may be carried out. Besides, the display can also be carried out over plural pages or plural screens. Further, at this time, the display section 230 maybe constructed such that it displays the judgment processing result as to whether or not the image of the calculation section 210 is suitable, and the operator can refer to it. Next, when the operator confirms the displayed image and selects the signal to be used as the measurement object by the input section 270, the calculation section 210 selects the first signal and the second signal corresponding to the selected signals as the first and the second measurement signals used for the subsequent calculation from the memory 240, and stores them, if necessary, in the memory 240 (S253). In case the signals are not selected by the predetermined number (for example, three, four, etc.) previously determined by the input section 27 or the like, the calculation section 210 returns to the step S251 and again carries out an image display (S235). On the other hand, when the predetermined number of the first and the second measurement signals are selected, the procedure proceeds to the subsequent calculation processing.

The calculation section 210 calculates, for example, the optical characteristics of the eye 60 to be measured with the first signal, and further, calculates the corneal shape of the eye 60 to be measured with the second signal (S223). The calculation section 210 stores the measurement result at the step S223 into the memory 240 (S224). Incidentally, each time the signal to be used is selected, the optical characteristics may be obtained on the basis of the signal. The calculation section 210 displays the measurement result stored in the memory 240 at the step S224 on the display section 230 (S225). Incidentally, at the step S225, in the case where the plural first and second signals are selected, images or data concerning the obtained plural ophthalmic characteristics may be displayed, or images or data after statistic processing such as averaging may be displayed. The calculation section 210 judges whether measurement by the foregoing processing is ended, and in the case where it is not ended, the procedure is again returned to the step S203 (S227).

(3) Third Embodiment

Figure 12:
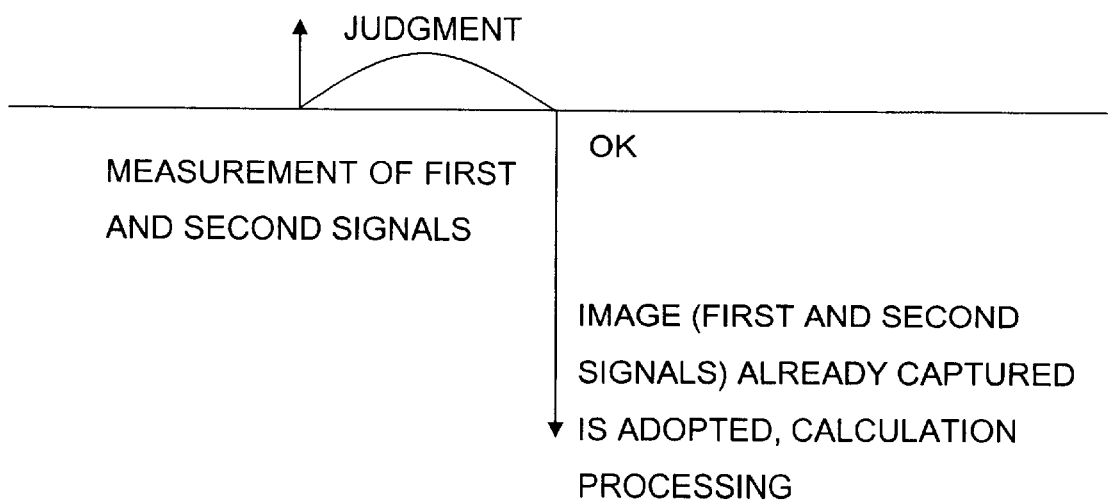
FIG. 12 is an explanatory view of a third embodiment relating to ophthalmic characteristic measurement.

FIG. 12 is an explanatory view of a third embodiment concerning ophthalmic characteristic measurement.

This third embodiment indicates the operation of a case where, for example, the first signal and the second are captured, and then, it is judged whether the first signal and/or the second signal can be used as the measurement object signal. The measurement object signal decision section 118 of the calculation section 210 checks, for example, the first and the second signals captured simultaneously or substantially simultaneously. When the measurement object signal decision section 118 judges that the signal measured on the basis of either one of or both of the signals can be used as the measurement object signal in accordance with the previously determined decision factor for measuring timing, both the signals are adopted, and the subsequent calculation processing of the ophthalmic characteristics is carried out.

Figure 13:
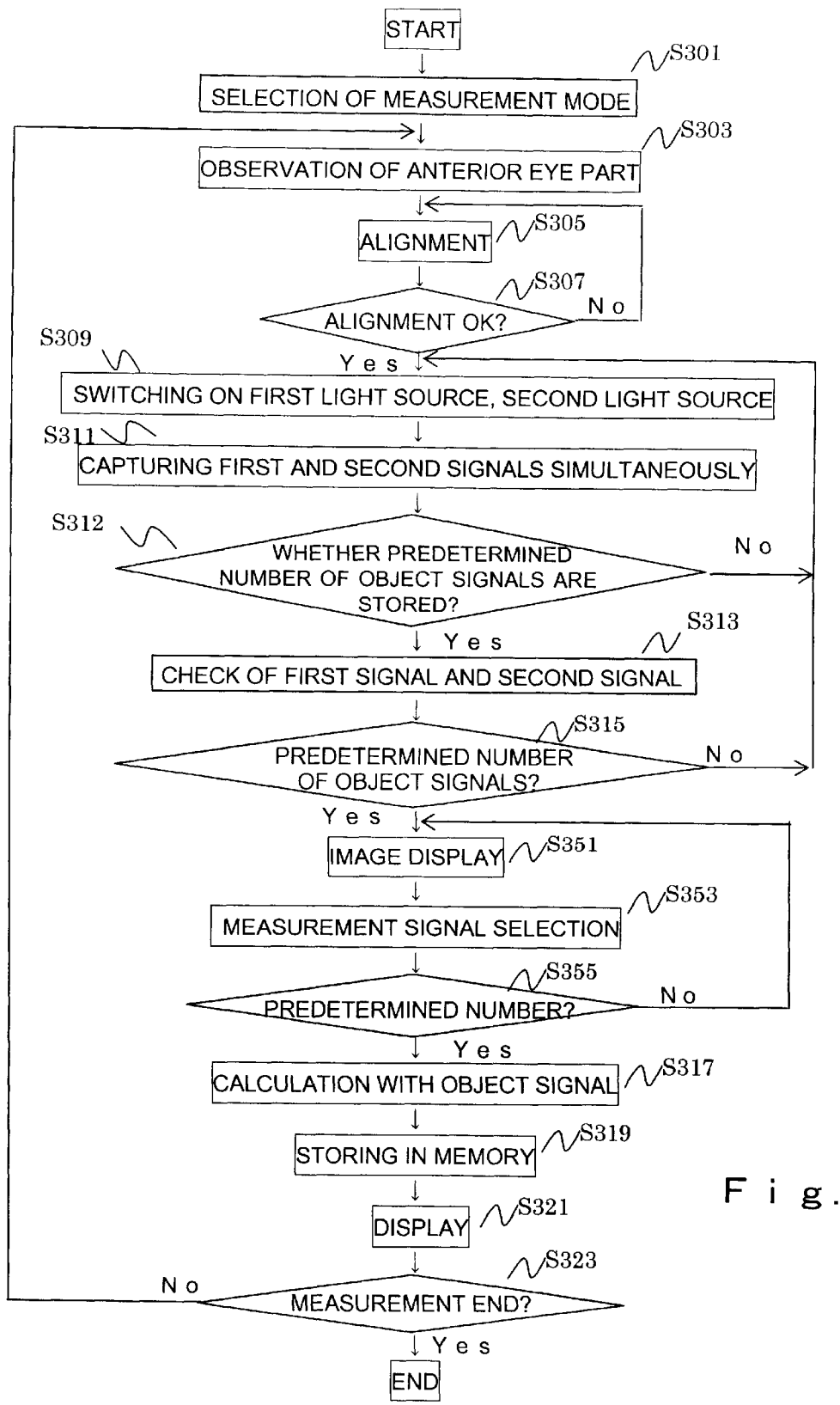
FIG. 13 is a flowchart of the third embodiment showing the operation of the ophthalmic optical characteristic measuring apparatus of the invention.

FIG. 13 is a flowchart of the third embodiment showing the operation of the ophthalmic optical characteristic measuring apparatus of the invention.

First, similarly to the first embodiment, the respective processings of selection of a measurement mode (S301), measurement of an anterior eye image (S303), and alignment (S305, S307) are carried out.

Next, the optical characteristic measuring apparatus 100 switches on the first light source and the second light source (S309). In accordance with the selected mode, the calculation section 210 captures the first and the second signals simultaneously or substantially simultaneously (S311). Here, the calculation section 210 captures one signal at a suitable timing or plural signals of both the signals continuously in the automatic mode, whereas in the manual mode, one or plural signals of both the signals are continuously captured by the measurement instructions of the operation. Next, the calculation section 210 judges whether the first signal and the second signal of the predetermined number of the object signals sufficient for the measurement are stored in the memory 240 (S312). The predetermined object signal is previously set by, for example, the input section 270. In the case where the predetermined number of the object signals are not stored in the memory 240 at the step S312, the calculation section 210 again returns to the step S309.

On the other hand, at step S312, in the case where the predetermined number of the object signals are stored in the memory 240 at the step S312, the measurement object signal decision section 118 of the calculation section 210 judges, for example, with the decision factor for measuring timing previously determined by the first signal and/or the second signal, whether or not the respective pairs of the captured first and second signals are suitable as the measurement objects (S313). Here, with respect to the decision factor for the object signals acquired at the step S313, the calculation section 210 judges whether the number of the object signals is the predetermined number (S315), and until the number of the object signals becomes the predetermined number, it returns to the step S309 and repeats the foregoing processing. Next, the measurement object signal decision section 118 of the calculation section 210 adopts one or plural object signals previously determined by the input section 270 or the like among the object signals stored in the memory 240.

Further, the calculation section 210 reads out the predetermined number of the first and second signals from the adopted object signals, and carries out an image display on the display section 230 (S351). At this time, as described above, the image to be displayed may be an image of one of the first signal and the second signal, or an image of both the signals. Besides, each time a measurement is made, an image display may be carried out. Besides, a display can also be carried out over plural pages or plural screens. Further, at this time, the display section 230 may be constructed such that the judgment processing result as to whether the image of the calculation section 210 is suitable is displayed, and the operator can refer to it. Next, when the operator confirms the displayed image and selects the signal to be used as the measurement object by the input section 270, the calculation section 210 selects the first signal and the second signal corresponding to the selected signals as the first and the second measurement signals used for the subsequent calculation from the memory 240, and stores, if necessary, them into the memory 240 (S353). In case where signals are not selected by the predetermined number (for example, three, four, etc.) previously determined by the input section 27 or the like, the calculation section 210 returns to the step S351 and again carries out an image display (S335) On the other hand, when the predetermined number of the first and second measurement signals are selected, the procedure proceeds to the subsequent calculation processing.

Subsequently, similarly to the foregoing embodiment, the calculation section 210 obtains the optical characteristics on the basis of the first and the second received light signals (S317). Next, the calculation section 210 calculates output data, stores it in the memory 240 (S319), displays it on the display section 230 (S321), and if necessary, outputs the output data. Incidentally, each time a signal to be used is selected, the optical characteristics may be obtained on the basis of the signal. Incidentally, at the step S321, in the case where the plural first and second signals are selected, images or data concerning the obtained plural ophthalmic characteristics may be displayed, or images or data after statistic processing such as averaging may be displayed. Thereafter, if the measurement is not completed, the processing is repeated, and if completed, the measurement is ended (S323).

(4) Fourth Embodiment

Figure 14:
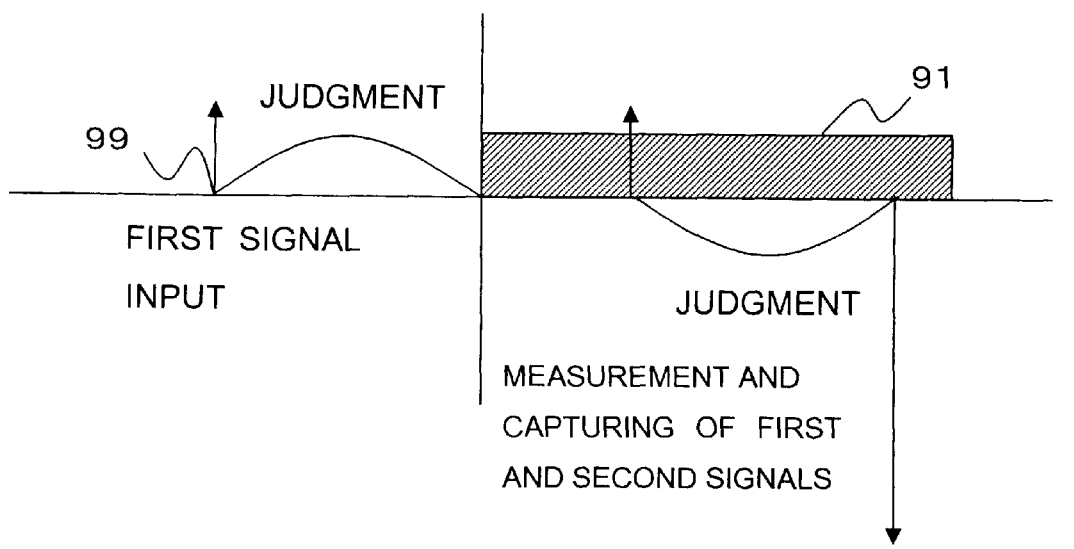
FIG. 14 is an explanatory view of a fourth embodiment relating to ophthalmic characteristic measurement.

FIG. 14 is an explanatory view of a fourth embodiment relating to ophthalmic characteristic measurement.

This fourth embodiment shows the operation of the case where a measurement timing is determined by the first signal, and a measurement object signal is determined after capturing the first signal and the second signal. The measurement timing decision section 117 of the calculation section 210 first receives the first signal to make a check in accordance with the decision factor for measuring timing. Incidentally, this check may be carried out with the second signal or both the signals. When it is judged by the measurement timing decision section 117 that a period is the measurable period, the measurement object signal decision section 118 of the calculation section 210 captures the first signal and the second signal in the measurable period 91 simultaneously or substantially simultaneously, and makes a measurement check of the first and the second signals. When the measurement object signal decision section 118 judges that signals measured on the basis of one of or both of the signals can be used as the measurement object signals in accordance with the previously determined decision factor for measuring timing, it adopts both the signals, and carries out the subsequent calculation processing of the ophthalmic characteristics.

Figure 15:
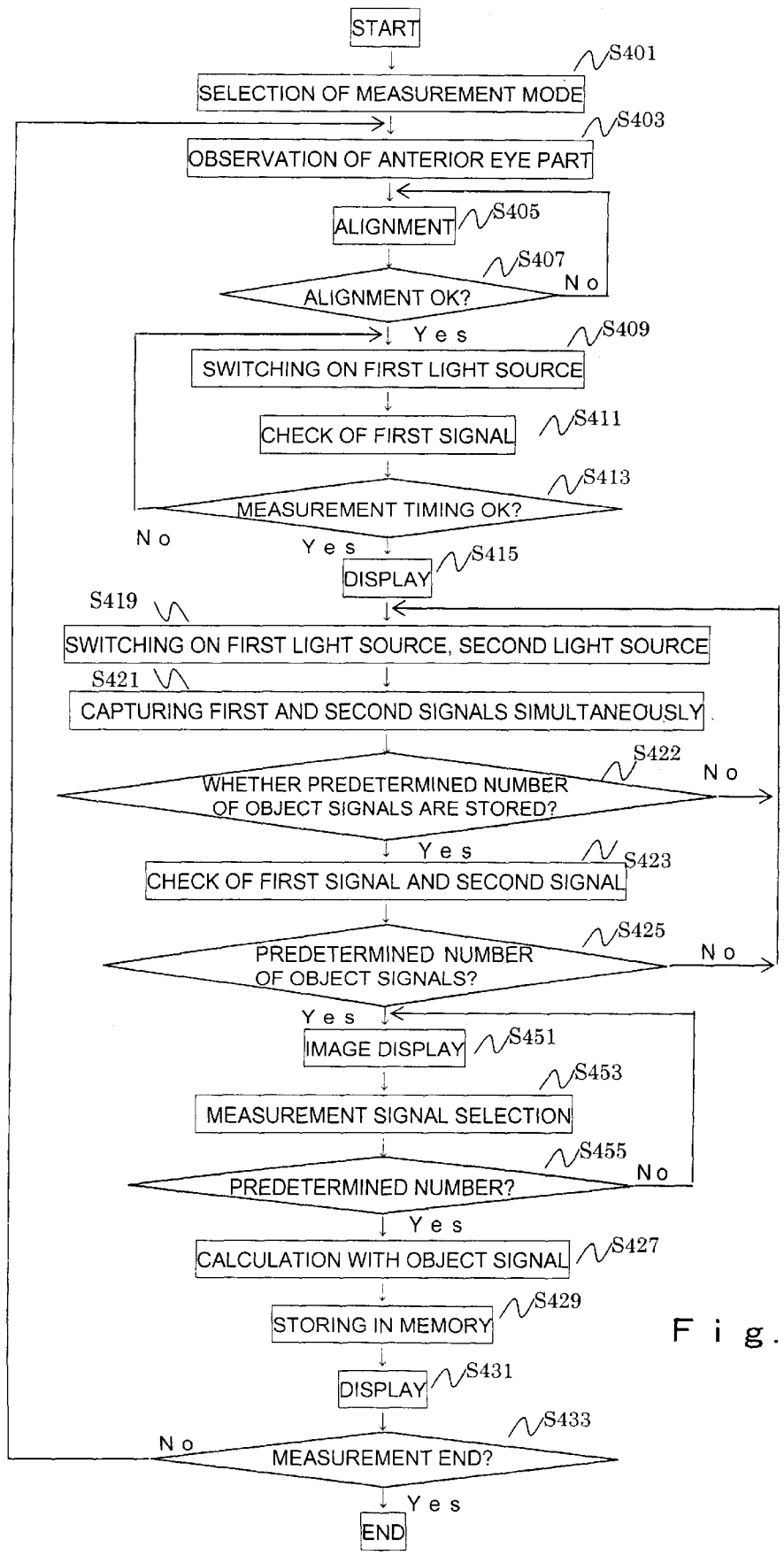
FIG. 15 is a flowchart of a fourth embodiment showing the operation of the ophthalmic optical characteristic measuring apparatus of the invention.

FIG. 15 is a flowchart of the fourth embodiment showing the operation of the ophthalmic optical characteristic measuring apparatus of the invention.

First, similarly to the first embodiment, the respective processings of selection of a measurement mode (S401), measurement of an anterior eye image (S403), and alignment (S405, S407) are carried out.

Next, the optical characteristic measuring apparatus 100 switches on the first light source in accordance with the first decision factor for measuring timing set by the input section 270 (S409). The measurement timing decision section 117 of the calculation section 210 judges whether the measurable period 91 as the period of measurement timing can be set in accordance with the decision factor for measuring timing (S411). When the measurement timing decision section 117 judges that a measurement can be made in accordance with the decision condition corresponding to the respective decision factors for measuring timing (S413), that the measurement can be made is displayed audibly or visibly by the display section 230 or the like (S415).

Next, similarly to the third embodiment, the optical characteristic measuring apparatus 100 switches on the first light source and the second light source (S419). In accordance with the mode set by the input section 270, the calculation section 210 captures the first and the second signals simultaneously or substantially simultaneously (S421) and judges whether the first and the second signals are stored in the memory 240 up to the predetermined number of object signals sufficient for measurement (S422). In the case where the predetermined number of object signals are not stored in the memory 240 at the step S422, the calculation section 210 again returns to the step S419.

On the other hand, in the case where the predetermined number of object signals are stored in the memory 240 at the step S422, the measurement object signal decision section 118 of the calculation section 210 judges whether or not the respective pairs of the captured first and second signals are suitable as measurement objects by the decision factor for measuring timing previously determined with the first signal and/or the second signal (S423). Here, with respect to the object signals acquired at the step S423, the calculation section 210 judges whether or not the number of the object signals is the predetermined number (S425), and until the number of the object signals becomes the predetermined number, it returns to the step S419 and repeats the foregoing processing. The measurement object signal decision section 118 of the calculation section 210 adopts one or plural object signals previously determined by the input section 270 or the like among the object signals stored in the memory 240.

Further, the calculation section 210 reads out the predetermined number of the first and second signals from the adopted object signals, and carries out an image display on the display section 230 (S451). At this time, as described above, an image to be displayed may be an image of one of the first signal and the second signal, or an image of both the signals. Besides, each time a measurement is made, an image display may be carried out. Besides, a display can also be carried out over plural pages or plural screens. Further, at this time, the display section 230 may be constructed such that the judgment processing result as to whether the image of the calculation section 210 is suitable is displayed, and the operator can refer to it. Next, when the operator confirms the displayed image, and selects signals to be used as measurement objects by the input section 270, the calculation section 210 selects the first signal and the second signal corresponding to the selected signals as the first and the second measurement signals used for the subsequent calculation from the memory 240, and stores, if necessary, them into the memory 240 (S453). In case a predetermined number (for example, three, four, etc.) of signals previously determined by the input section 27 or the like are not selected, the calculation section 210 returns to the step S451 and again carries out the image display (S435). On the other hand, when the predetermined number of the first and second measurement signals are selected, the procedure proceeds to the subsequent calculation processing.

Subsequently, similarly to the foregoing embodiment, the calculation section 210 obtains the optical characteristics on the basis of the first and the second received light signals (S427). Incidentally, each time a signal to be used is selected, the optical characteristics may be obtained on the basis of the signal. Next, the calculation section 210 calculates the output data, stores it in the memory 240 (S429), displays it on the display section 230 (S431), and outputs, if necessary, these output data. Incidentally, at the step S431, in the case where the plural first and second signals are selected, the images or data concerning the obtained plural ophthalmic characteristics may be displayed, or the image or data after statistic processing such as averaging may be displayed. Thereafter, if measurement is not completed, the processing is repeated, and if completed, the measurement is ended (S433).

According to the invention, as described above, it is possible to provide the ophthalmic characteristic measuring apparatus in which the first signal and the second signal are captured at the same time, and the optical characteristics of the eye to be measured and the corneal shape thereof can be measured at the same time. Besides, according to the invention, the first signal and the second signal can be captured at the same time or continuously. Besides, according to the invention, in view of the influence of the state of the first signal and the second signal exerted on the measurement, a measurement can be made when the state of the first signal and the second signal becomes such a state that highly reliable measurement result can be obtained.

Besides, according to the invention, the suitableness of plural factors exerting influence on the measurement are judged, and the suitable measurement timing can be determined. Besides, according to the invention, the first signal and the second signal can be simultaneously continuously captured plural times. Besides, according to the invention, the timing of capturing the first signal and the second signal suitable for measurement can be decided.

What is claimed is:

1. An ophthalmic characteristic measuring apparatus, comprising:

a first light source for emitting a first light flux of a first wavelength of near infrared;

a first illumination optical system for illuminating a minute region on a retina of a subject eye with the light flux from the first light source;

a first light receiving optical system for receiving a part of a first reflected light flux of the first light flux from the first light source, reflected from the retina of the subject eye, through a first conversion member for converting it into at least 17 beams;

a first light receiving section for receiving a first received light flux guided by the first light receiving optical system to form a first signal;

a second light source section for emitting a second light flux of near infrared having a second wavelength longer than the first wavelength of the first light flux;

a second illumination optical system for illuminating a vicinity of the cornea of the subject eye with the second light flux from the second light source and with a predetermined pattern;

a second light receiving optical system for receiving a second reflected light flux of the second light flux from the second light source, reflected from the vicinity of the cornea of the subject eye;

a second light receiving section for receiving a second received light flux guided by the second light receiving optical system to form a second signal;

a display section for displaying, as an image, the first and/or the second signal from the first light receiving section and/or the second light receiving section;

an input section for selecting the first and/or the second signal used for a calculation processing on the basis of an image display of the first and/or the second signal displayed on the display section; and a calculation section for obtaining optical characteristics of the subject eye and a corneal shape of the subject eye on the basis of first and second signals corresponding to the first and/or second signal selected by the input section.

2. An ophthalmic characteristic measuring apparatus according to claim 1, wherein:

the display section displays, as an image, one of the first signal of the first light receiving section and the second signal of the second light receiving section;

the input section selects the signal used for the calculation processing from the image display of one of the signals displayed on the display section; and the calculation section obtains, on the basis of the signal selected by the input section, the optical characteristics of the subject eye and the corneal shape of the subject eye using the selected one signal and the other signal measured at the same timing or substantially the same timing.

3. An ophthalmic characteristic measuring apparatus according to claim 1, wherein:

the display section displays, as images, the first and the second signals of the first light receiving section and the second light receiving section;

the input section selects the first and the second signals used for the calculation processing from the image display of the first and the second signals displayed on the display section; and the calculation section obtains, on the basis of the first and the second signals selected by the input section, the optical characteristics of the subject eye and the corneal shape of the subject eye.

4. An ophthalmic characteristic measuring apparatus according to claim 1, wherein:

the calculation section carries out a judgment processing for judging whether the first and the second signals of the first light receiving section and the second light receiving section are suitable for the processing in the calculation section;

the display section displays a judgment processing result of the calculation section;

the input section selects, on the basis of the judgment processing result displayed on the display section, the first and/or the second signal used for a measurement calculation processing; and the calculation section obtains the optical characteristics of the subject eye and the corneal shape of the subject eye on the basis of the first and the second signals corresponding to the first and/or the second measurement signal selected by the input section.

5. An ophthalmic characteristic measuring apparatus according to claim 1, wherein the calculation section captures the first and the second signals from the first light receiving section and the second light receiving section at the same timing or substantially the same timing, obtains the optical characteristics of the subject eye on the basis of the first signal from the first light receiving section, and obtains the corneal shape of the subject eye on the basis of the second signal from the second light receiving section.

6. An ophthalmic characteristic measuring apparatus according to claim 1, wherein the calculation section comprises a measurement object signal decision section for determining the first signal and the second signal as objects for which a measurement calculation is carried out.

7. An ophthalmic characteristic measuring apparatus according to claim 6, wherein the measurement object signal decision section judges, on the basis of the first signal and/or the second signal, suitableness with a predetermined decision factor for measuring timing, and in accordance with this, decides a measurement object signal of the first signal and the second signal.

8. An ophthalmic characteristic measuring apparatus according to claim 7, wherein the predetermined decision factor for measuring timing is at least one of fixation state, a blink, a poor tear film, a lack of a pupil diameter, and a poor opening eyelid.

9. An opthalmic characteristic measuring apparatus according to claim 1, wherein the calculation section comprises a measurement timing decision section for deciding, on the basis of the first and/or the second signal, a measurement timing of the first signal and the second signal as objects for which a measurement operation is carried out.

10. An opthalmic characteristic measuring apparatus according to claim 9, wherein the measurement timing decision section uses, as the predetermined decision factor for measuring timing, at least one of a blink, a poor tear film, a lack of a pupil diameter, and a poor opening eyelid.

* * * * *